(12) United States Patent
Hess et al.

(10) Patent No.: US 10,299,785 B2
(45) Date of Patent: May 28, 2019

(54) SURGICAL ACCESS DEVICES WITH INTEGRATED WOUND CLOSURE FEATURES

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Jerome R. Morgan, Cincinnati, OH (US); Ryan A. Bledsoe, Cincinnati, OH (US); Douglas E. Withers, Cincinnati, OH (US); Craig T. Gates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/088,723

(22) Filed: Apr. 1, 2016

(65) Prior Publication Data

US 2017/0281154 A1    Oct. 5, 2017

(51) Int. Cl.
*A61B 17/04* (2006.01)
*A61B 17/02* (2006.01)
(Continued)

(52) U.S. Cl.
CPC ...... *A61B 17/0469* (2013.01); *A61B 17/0057* (2013.01); *A61B 17/0218* (2013.01); *A61B 17/0482* (2013.01); *A61B 17/3417* (2013.01); *A61B 17/3421* (2013.01); *A61B 17/3423* (2013.01); *A61B 17/3439* (2013.01); *A61B 17/3462* (2013.01); *A61M 39/04* (2013.01); *A61B 2017/00637* (2013.01);
(Continued)

(58) Field of Classification Search
CPC ...... A61B 17/0482; A61B 2017/00637; A61B 17/0057; A61B 17/0469; A61B 1/313
See application file for complete search history.

(56) References Cited

U.S. PATENT DOCUMENTS 5,391,182 A    2/1995 Chin
5,476,470 A    12/1995 Fitzgibbons, Jr.
(Continued)

OTHER PUBLICATIONS

US 5,183,485 A1, 02/2001, Thomason et al. (withdrawn)
(Continued)

*Primary Examiner* — Lynnsy M Summitt
(74) *Attorney, Agent, or Firm* — Frost Brown Todd LLC

(57) ABSTRACT

Surgical access devices having wound closure features incorporated as part of the device are provided. The devices allow suture to be inserted directly into the device and operated to close an opening through which the device is disposed as or shortly after the device is removed from the surgical site. Further, the wound closure features allow for various orientations of wound closure to be achieved by adjusting an angle at which the suture enters tissue surrounding the opening to be closed. Some of the wound closure features provided for include openings formed in both the housing and cannula of the surgical access device, multiple openings formed in one or both the housing and cannula, locations of the openings being adjustable or otherwise movable, and various flexible seals. Other features, as well as methods of closing an opening through which the surgical access device was disposed, are also provided.

27 Claims, 23 Drawing Sheets

(51) Int. Cl.
 *A61B 17/34* (2006.01)
 *A61B 17/00* (2006.01)
 *A61M 39/04* (2006.01)

(52) U.S. Cl.
 CPC .............. *A61B 2017/00663* (2013.01); *A61B 2017/0225* (2013.01); *A61B 2017/3441* (2013.01); *A61B 2017/3445* (2013.01); *A61B 2017/3464* (2013.01)

(56) References Cited

U.S. PATENT DOCUMENTS

| | | | |
|---|---|---|---|
| 5,507,755 A | 4/1996 | Gresl et al. | |
| 5,507,758 A | 4/1996 | Thomason et al. | |
| 5,562,688 A * | 10/1996 | Riza | A61B 17/0469 606/139 |
| 5,716,369 A * | 2/1998 | Riza | A61B 17/0469 606/139 |
| 5,782,845 A | 7/1998 | Shewchuk | |
| 5,830,232 A | 11/1998 | Hasson | |
| 5,984,948 A | 11/1999 | Hasson | |
| 5,993,471 A * | 11/1999 | Riza | A61B 17/3498 606/185 |
| 7,981,092 B2 | 7/2011 | Duke | |
| 8,177,762 B2 | 5/2012 | Beasley et al. | |
| 8,465,476 B2 | 6/2013 | Rogers et al. | |
| 8,475,490 B2 | 7/2013 | Hess | |
| 8,518,059 B2 | 8/2013 | Ringley | |
| 8,545,522 B2 | 10/2013 | Shpaichler et al. | |
| 8,568,362 B2 | 10/2013 | Moreno, Jr. et al. | |
| 8,579,807 B2 | 11/2013 | Moreno, Jr. et al. | |
| 8,622,970 B2 | 1/2014 | Wingardner, III et al. | |
| 8,623,028 B2 | 1/2014 | Rogers et al. | |
| 8,636,686 B2 | 1/2014 | Minnelli et al. | |
| 8,690,831 B2 | 4/2014 | Duke | |
| 8,821,391 B2 | 9/2014 | Widenhouse et al. | |
| 8,906,042 B2 | 12/2014 | Hodgkinson et al. | |
| 8,915,932 B2 | 12/2014 | Pipenhagen et al. | |
| 8,926,639 B2 | 1/2015 | Bagaoisan et al. | |
| 8,979,747 B2 | 3/2015 | Auerbach et al. | |
| 8,992,549 B2 | 3/2015 | Bennett, III | |
| 9,011,319 B2 | 4/2015 | Norton et al. | |
| 9,033,872 B2 | 5/2015 | Mohajer-Shojaee | |
| 9,066,717 B2 | 6/2015 | Sherts et al. | |
| 9,510,823 B2 | 12/2016 | Malkowski | |
| 9,636,104 B2 | 5/2017 | Mohajer-Shojaee | |
| 9,687,270 B2 * | 6/2017 | Gaiselmann | A61B 17/3417 |
| 9,700,303 B2 * | 7/2017 | Prior | A61M 5/329 |
| 2004/0068273 A1 | 4/2004 | Fariss et al. | |
| 2007/0203507 A1 | 8/2007 | McLaughlin et al. | |
| 2008/0033459 A1 | 2/2008 | Shafi et al. | |
| 2008/0097485 A1 * | 4/2008 | Shpaichler | A61B 17/0482 606/148 |
| 2011/0082475 A1 * | 4/2011 | Smith | A61B 17/0057 606/144 |
| 2011/0112557 A1 * | 5/2011 | Beeley | A61B 17/0057 606/148 |
| 2012/0265223 A1 * | 10/2012 | Shpaichler | A61B 17/0482 606/148 |
| 2013/0035699 A1 | 2/2013 | Heneveld et al. | |
| 2013/0035700 A1 | 2/2013 | Heneveld | |
| 2013/0035701 A1 | 2/2013 | Heneveld et al. | |
| 2013/0035702 A1 | 2/2013 | Heneveld | |
| 2013/0079597 A1 * | 3/2013 | Auerbach | A61B 17/0482 600/204 |
| 2013/0103057 A1 | 4/2013 | Keating et al. | |
| 2013/0165956 A1 * | 6/2013 | Sherts | A61B 17/0482 606/148 |
| 2013/0253543 A1 | 9/2013 | Heneveld | |
| 2014/0163323 A1 * | 6/2014 | Mohajer-Shojaee | A61B 17/0057 600/204 |
| 2015/0038793 A1 | 2/2015 | Prior et al. | |
| 2015/0038994 A1 * | 2/2015 | Prior | A61M 5/329 606/147 |
| 2015/0038997 A1 | 2/2015 | Malkowski et al. | |
| 2015/0094741 A1 | 4/2015 | Hodgkinson et al. | |
| 2015/0119906 A1 | 4/2015 | Bagaoisan et al. | |
| 2016/0045224 A1 | 2/2016 | Hendershot, III | |
| 2017/0258466 A1 | 9/2017 | Prior et al. | |

OTHER PUBLICATIONS

U.S. Appl. No. 15/274,182.
U.S. Appl. No. 15/274,198.
U.S. Appl. No. 15/274,209.
U.S. Appl. No. 15/274,237.
International Search Report and Written Opinion dated Jun. 19, 2017 for Application No. PCT/US2017/024691, 17 pgs.
European Search Report and Written Opinion dated Aug. 23, 2017 for Application No. EP 17164122.8, 7 pgs.

\* cited by examiner

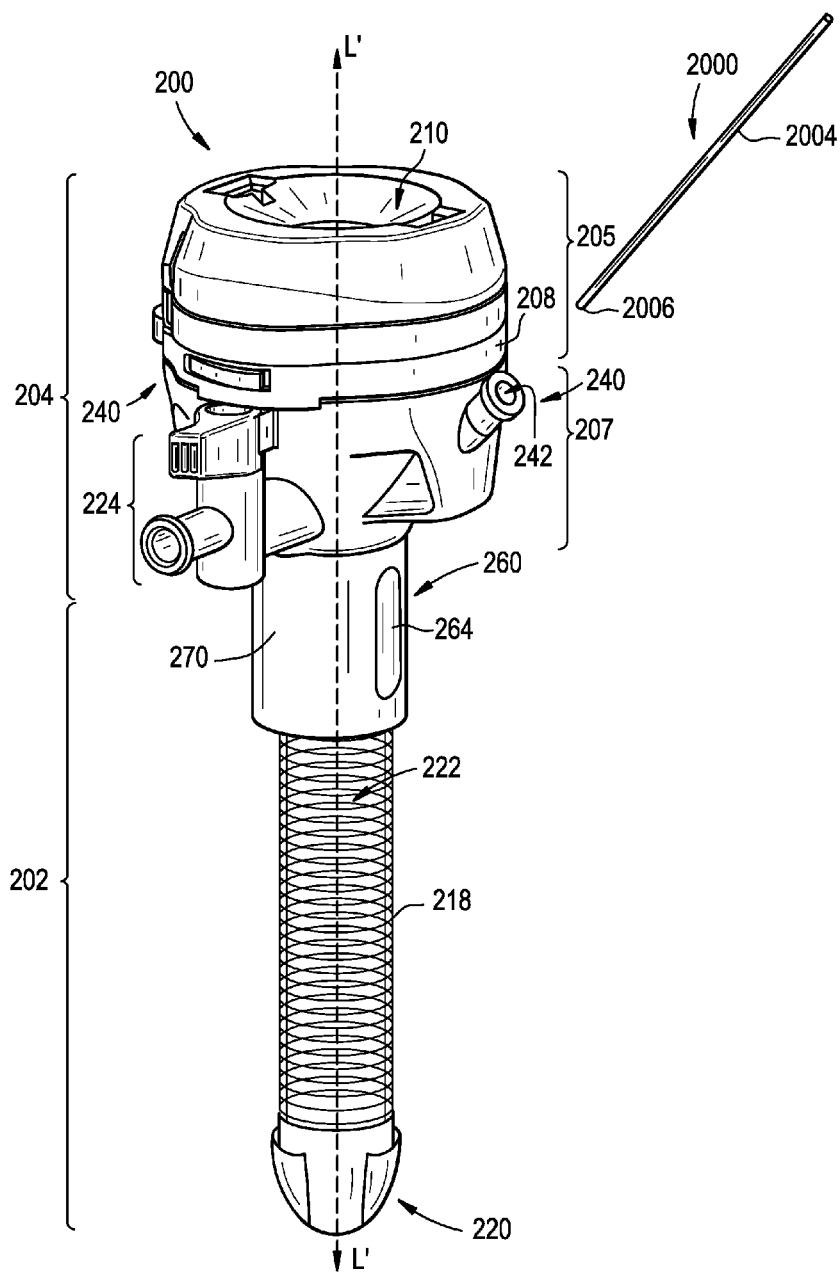

SURGICAL ACCESS DEVICES WITH INTEGRATED WOUND CLOSURE FEATURES

FIELD

The present disclosure relates to surgical access devices, and more particularly provides for features incorporated into surgical access devices that assist in closing an opening in which the surgical access device is disposed while or shortly after the surgical access device is removed from the surgical site. The disclosure also pertains to methods related to the same.

BACKGROUND

Surgical procedures often require a surgeon to gain access to a cavity in a patient's body. Generally, when such a procedure is required, an incision is made in an exterior wall of the cavity and an instrument is inserted into the working channel created by the incision. One common instrument used in such a procedure is a trocar assembly. Trocar assemblies include a variety of components, but generally can include a trocar cannula, a trocar obturator, and a trocar housing. In many designs, in order to access the body cavity, the trocar cannula is directed through the skin and the trocar obturator is inserted through an interior lumen defined by the cannula. The trocar obturator is then used to penetrate the skin, which has often already had an incision made in it with a scalpel or similar device, and access the body cavity. More specifically, in some designs, applying pressure against a proximal end of the trocar obturator allows a sharp point at a distal end of the trocar obturator to be forced through the skin until it enters the body cavity. Then, the trocar cannula is inserted through the perforation made by the trocar obturator and the trocar obturator is withdrawn, leaving the inner lumen of the trocar cannula as a path to access the body cavity from outside of the body.

The trocar housing can be joined to a proximal end portion of the trocar cannula, and further, the housing can define a working chamber with an open distal end portion that is in communication with the interior lumen of the cannula. Just as the interior lumen can receive the obturator, it can also receive other elongated surgical instruments such that the instruments can be axially extended into and withdrawn from the cannula through the proximal end portion of the working chamber defined by the trocar housing. For example, in order to allow a surgeon to more easily see during a procedure, an endoscope can be inserted through the cannula and proximal or into the body cavity. Further, it is common for one or more seals to be disposed within the housing and/or the cannula to help prevent fluid or gas from escaping during surgical procedures. Such prevention is needed, especially during certain minimally invasive surgical procedures, in which an insufflations gas is used to expand a body cavity. In many instances, at least two seals are used to help maintain a seal while instruments are passed into and out of the working channel.

Once a procedure is completed, the trocar is removed and the opening (sometimes referred to herein as a wound) that was formed through which the trocar is inserted is typically closed. The size of the opening will depend on the size of the trocar. Some common trocar sizes include trocars identified as 5 millimeter trocars, 8 millimeter trocars, 12 millimeter trocars, and 15 millimeter trocars, with the size correlating approximately to the inner diameter of the cannula. At least for openings that are 8 millimeters wide or larger, suture is typically used to close the opening to prevent hernations after surgery. The stitching of the opening is typically done after the trocar is removed, or at least a housing portion of the trocar, and thus the ability to insufflate at that point is lost. The stitching up process typically involves using additional tools and performing several extra steps after the primary surgical method has already been completed. This leads to increased difficulty in closing the opening, an increased amount of time to perform the surgery, and a greater likelihood for unnecessary trauma to the tissue surrounding the opening. It can be particularly tough to stitch the opening when the cavity wall in which the opening is formed is thick, e.g., approximately equal to or greater than three-quarters of an inch, as is often the case for abdominal walls.

Accordingly, there is a need to reduce or eliminate the need for extra tools to be used to close an opening through which a trocar is passed during a surgical procedure, and to reduce the amount of steps required to close the opening. The solution should provide for a more convenient and easier way for surgeons to close the opening and reduce possible trauma to the surround tissue and the patient generally.

SUMMARY

Surgical access devices that incorporate wound closure features (or opening closure features) to allow an opening through which the surgical access device is passed to be closed while or shortly after the surgical access device is withdrawn from the opening are provided for in the present disclosure. Various configurations provide for sealed openings associated with a housing or proximal end of a surgical access device, as well as sealed openings associated with a cannula of the surgical access device. There can be multiple openings associated with each of the housing and the cannula, which thus make the wound closure feature adjustable. By passing a suture through different openings, the angle at which a suture passes through tissue can be changed. As this angle, referred to herein as a bite angle, is adjusted, in impacts the amount of tissue through which the suture passes and provides for various configurations to close the opening. The adjustability of the bite angle can be further enhanced by providing for openings that are movable or are otherwise adjustable as provided for in the present disclosure. For example, one or more of the openings can be rotated around a central longitudinal axis of the surgical access device, and/or the opening itself can provide for some adjustability by being flexible and/or by providing for an instrument-receiving opening that is smaller than the opening itself. When the instrument-receiving opening is smaller than the opening itself, the instrument-receiving opening can be moved with respect to the opening itself to adjust the angle at which an instrument disposed in the instrument-receiving opening passes through the opening. Still further, the present disclosure also provides for seals that include a patterned guide surface conducive to both position and locate a surgical instrument passed therethrough to a desired position. The seals are also resistant to tearing, thereby preventing undesirable remnants of the seal from entering the body.

In one exemplary embodiment, a surgical access device includes a housing and a cannula extending distally from the housing. The housing has a central lumen extending through it and a sidewall disposed around the central lumen, while the cannula is in fluid communication with the central lumen to define a working channel that is sized and configured to receive a surgical instrument. The sidewall of the housing has at least one opening extending through it, with that opening having an opening seal associated with it, and the cannula has at least one sealed opening extending through a sidewall of the cannula. A seal is disposed within the working channel. The seal is configured to seal the working channel when no surgical instrument is disposed through the seal. The opening(s) extending through the sidewall of the housing and the sealed opening(s) extending through the sidewall of the cannula are configured to form a suture path(s). A suture path allows a suture to be passed from an outside environment, through the at least opening of the housing, through the at least one sealed opening of the cannula, and to a surgical site.

The at least one opening that extends through the housing sidewall and the at least one sealed opening that extends through the cannula sidewall can be configured such that an angle formed between a central longitudinal axis extending through the cannula and an axis extending between the at least one opening extending through the housing sidewall and the at least one sealed opening extending through the cannula sidewall is adjustable. A variety of different features that permit the adjustability of this angle, sometimes referred to as a bite angle, are provided for in the present disclosure. For example, the housing sidewall can include a plurality of openings that extend through the housing sidewall, with each opening having a seal associated with it. In such instances, the angle is adjustable at least by virtue of the axis extending between the openings of the housing sidewall and the cannula sidewall passing through different openings of the plurality of openings that extend through the housing sidewall. For instance, in a first position, the axis extending between the openings of the housing sidewall and the cannula sidewall can extend between a first opening of the plurality of openings extending through the housing sidewall and an opening of the at least one sealed opening extending through the cannula sidewall, and in a second position the same axis can extend between a second opening of the plurality of openings extending through the housing sidewall and the opening of the at least one sealed opening extending through the cannula sidewall.

By way of further example, adjustability of the bite angle can be provided for by the cannula sidewall including a plurality of sealed openings that extend through the cannula sidewall. In such instances, the angle is adjustable at least by virtue of the axis extending between the openings of the housing sidewall and the cannula sidewall passing through different sealed openings of the plurality of sealed openings that extend through the cannula sidewall. For instance, in a first position, the axis extending between the openings of the housing sidewall and the cannula sidewall can extend between an opening of the at least one opening extending through the housing sidewall and a first sealed opening of the plurality of sealed openings extending through the cannula sidewall, and in a second position the same axis can extend between the opening of the at least one opening extending through the housing sidewall and a second sealed opening of the plurality of sealed openings extending through the cannula sidewall.

By way of still further example, adjustability of the bite angle can be provided for by one or more elongate openings. The at least one opening extending through the housing sidewall can include an elongate opening having an elongate length that extends substantially parallel to the central longitudinal axis. The elongate opening can further include an adjustable entry point that is movable along the elongate length to adjust the angle formed between the central longitudinal axis and the axis extending between the elongate opening and the at least one sealed opening of the cannula sidewall.

By way of yet another example, adjustability of the bite angle can be provided by a housing that includes a first rotary disc and a second rotary disc that are each configured to rotate about the central longitudinal axis extending through the cannula. Further, each disc can include one or more openings of the opening(s) that extend through the housing sidewall disposed on the respective discs, with the opening disposed on the first disc being referred to at least in this instance as a first opening and the opening disposed on the second disc being referred to at least in this instance as a second opening. The first and second openings can be movable, e.g., by rotating them about the central longitudinal axis, to adjust the angle formed between the central longitudinal axis extending through the cannula and the axis extending between the openings of the housing sidewall and the cannula sidewall.

In some embodiments that include the first and second rotary discs, the first and second openings can be configured to be moved to an alignment position in which the first and second openings are aligned to form an elongate opening having an elongate length that extends substantially parallel to the central longitudinal axis. The elongate opening can be configured to allow for multiple entry points of a surgical instrument to provide the adjustable angle formed between the central longitudinal axis and the axis extending between the openings of the housing sidewall and the cannula sidewall.

By way of another example, adjustability of the bite angle can be controlled by a rotary dial. The rotary dial can be configured to move the at least one opening extending through the housing sidewall. The movement of this opening adjusts the angle formed between the central longitudinal axis and the axis extending between the openings extending through the housing sidewall and the cannula sidewall.

The various embodiments described with respect to the adjustability of the bite angle can be combined. By way of non-limiting example, both the housing sidewall and the cannula sidewall can include multiple openings, any of which can be elongate openings that do or do not have adjustable entry points. By way of further non-limiting example, any number of openings formed in the sidewall of the housing can be formed on one or more rotary discs. By way of still a further non-limiting example, a rotary dial can be used to control components such as rotary discs and/or adjustable entry points of elongate openings, among other features. The angle formed by the central longitudinal axis and the axis extending between the openings of the housing sidewall and the cannula sidewall in any of the provided for embodiments can be adjusted between values approximately in the range of about 15 degrees to about 60 degrees. The angle formed allows different wall thicknesses to be passed through. Accordingly, in view of the present disclosures, a range of wall thicknesses through which an instrument and/or a suture can be passed in view of the provided for surgical access devices is approximately in the range of about 1 centimeter to about 5 centimeters.

In some embodiments, the at least one sealed opening of the cannula sidewall can include a seal having a patterned guide surface that faces towards the working channel. The patterned guide surface can be configured to direct a surgical instrument through one or more pre-defined resealable openings of the seal. The patterned guide surface can include a slidable, floating instrument that allows an angle formed between a central longitudinal axis extending through the cannula and an axis extending between the at least one opening of the housing sidewall and the at least one sealed opening of the cannula sidewall to be adjustable.

A proximal portion of the cannula can have a portion of its sidewall that is thinner than surrounding portions of the cannula sidewall. Further, the thinner portion can have at least one sealed opening that extends through the cannula sidewall. In such embodiments, a sealing sleeve that is sized to be disposed over the thinner portion can be included. The sealing sleeve can be sized such that an outer diameter of the combination of the thinner portion of the sidewall and the sealing sleeve is substantially similar to an outer diameter of the surrounding portions of the cannula sidewall. The sealing sleeve can then provide the sealable nature of the at least one sealed opening of the surgical access device.

In another exemplary embodiment, a surgical access device includes a housing, a cannula extending distally from the housing, a seal, at least one entry port, and at least one sealed exit port. The housing and the cannula define a working channel that extends through the two components, with the working channel being sized and configured to receive a surgical instrument. The seal is disposed within the working channel, and is configured to seal the working channel when no instrument is disposed in it. The at least one entry port is disposed in or proximate to the housing, and has a seal associated with the entry port. The at least one sealed exit port extends through a sidewall of the cannula. Further, the entry and exit ports are configured such that an angle formed between a central longitudinal axis that extends through the cannula and an axis that extends between the ports, i.e., the bite angle, is adjustable.

The angle formed between the central longitudinal axis and the axis that extends between the ports can be adjustable approximately between the values of about 15 degrees to about 60 degrees. The angle formed allows different wall thicknesses to be passed through. Accordingly, in view of the present disclosures, a range of wall thicknesses through which an instrument and/or a suture can be passed in view of the provided for surgical access devices is approximately in the range of about 1 centimeter to about 5 centimeters. In some embodiments, the at least one entry port can include a plurality of entry ports disposed in or proximate to the housing, with each opening having a seal associated with it. In such instances, the angle is adjustable at least by virtue of the axis extending between the entry and exit ports passing through different entry ports of the plurality of entry ports. For instance, in a first position, the axis extending between the entry and exit ports can extend between a first entry port of the plurality of entry ports and an exit port of the at least one sealed exit port, and in a second position the same axis can extend between a second entry port of the plurality of entry ports and the exit port of the at least one sealed exit port.

In some embodiments, the at least one sealed exit port can include a plurality of sealed exit ports that extend through the sidewall of the cannula. In such instances, the angle is adjustable at least by virtue of the axis extending between the entry and exit ports passing through different sealed exit ports of the plurality of sealed exits ports. For instance, in a first position, the axis extending between the entry and exit ports can extend between an entry port of the at least one entry port and a first sealed exit port of the plurality of sealed exit ports, and in a second position the same axis can extend between the entry port of the at least one sealed entry port and a second sealed exit port of the plurality of sealed exit ports.

The at least one entry port can include an elongate opening having an elongate length that extends substantially parallel to the central longitudinal axis. The elongate opening can further include an adjustable entry point that is movable along the elongate length to adjust the angle formed between the central longitudinal axis and the axis extending between the elongate opening and the at least one sealed exit port.

The housing can sometimes include both a first rotary disc and a second rotary disc, with each disc being configured to rotate about the central longitudinal axis that extends through the cannula. The first rotary disc can have disposed on it a first entry port of the at least one entry port that is disposed in or proximate to the housing, and the second rotary disc can likewise have disposed on it a second entry port of the at least one entry port that is disposed in or proximate to the housing. The first and second entry ports can be movable to adjust the angle formed between the central longitudinal axis and the axis extending between the entry and exit ports.

In some embodiments that include the first and second rotary discs, the first and second entry ports can be moved to an alignment position in which the first and second entry ports are aligned to form an elongate opening having an elongate length that extends substantially parallel to the central longitudinal axis. The elongate opening can be configured to allow for multiple entry points of a surgical instrument to provide the adjustable angle formed between the central longitudinal axis and the axis extending between the entry and exit ports.

In some embodiments, a rotary dial can be included to assist in adjusting the bite angle. The rotary dial can be configured to move the at least one entry port. The movement of the entry port adjusts the angle formed between the central longitudinal axis and the axis extending between the entry and exit ports.

Again, the various embodiments described with respect to different ways by which the bite angle can be adjusted can be combined. By way of non-limiting example, there can be multiple entry ports and exit ports, any of which can include elongate openings that do or do not have adjustable entry points. By way of further non-limiting example, any number of entry ports can be formed on one or more rotary discs. By way of still a further non-limiting example, a rotary dial can be used to control components such as rotary discs and/or adjustable entry points of elongate openings, among other features.

In some embodiments, the at least one sealed exit port can include a seal having a patterned guide surface that faces towards the working channel. The patterned guide surface can be configured to direct a surgical instrument through one or more pre-defined resealable openings of the seal. The patterned guide surface can include a slidable, floating instrument entrance that allows an angle formed between the central longitudinal axis and the axis extending between the entry and exit ports to be adjustable.

A proximal portion of the cannula can have a portion of its sidewall that is thinner than surrounding portions of the cannula sidewall. Further, the thinner portion can have at least one sealed exit port that extends through the cannula sidewall. In such embodiments, a sealing sleeve that is sized to be disposed over the thinner portion can be included. The sealing sleeve can be sized such that an outer diameter of the combination of the thinner portion of the sidewall and the sealing sleeve is substantially similar to the outer diameter of the surrounding portions of the cannula sidewall. The sealing sleeve can then provide the sealable nature of the at least one sealed exit port of the surgical access device.

An exemplary embodiment of a surgical method includes passing a first filament tail through a first opening extending through a sidewall of a housing of a surgical access device, through a first opening extending through a sidewall of a cannula that extends distally from the housing, and through tissue adjacent to an opening in tissue. The method further includes passing a second filament tail through a second opening extending through the sidewall of the housing of the surgical access device, through a second opening extending through the sidewall of the cannula, and through tissue adjacent to the opening in the tissue. Tension is applied to at least one of the first and second filament tails, which in turn decreases a size of the opening in the tissue.

In some embodiments, the steps of passing the first and second filament tails through first and second openings extending through the housing sidewall, respectively, can include selecting one opening of a plurality of openings that extend through the housing sidewall and are proximate to each other to be the respective first or second opening based on the desired angle at which the respective first or second filament tail is to be passed through the tissue. Likewise, in some embodiments, the steps of passing the first and second filament tails through first and second openings extending through the cannula sidewall, respectively, can include selecting one opening of a plurality of openings that extend through the cannula sidewall to be the respective first or second opening based on the desired angle at which the respective first or second filament tail is to be passed through the tissue.

The at least one of the first and second openings that extend through the housing sidewall can include an elongate opening having an elongate length that extends substantially parallel to a central longitudinal axis that extends through the cannula. The elongate opening can further include an adjustable entry point that is movable along the elongate length. In such embodiments, the method can include moving the adjustable entry point longitudinally to adjust an angle at which the respective first or second filament tail is directed to enter the tissue. Further, the surgical method can include moving at least one of the first and second openings that extend through the housing sidewall to adjust an angle at which the respective first or second filament tail is directed to enter the tissue.

In one exemplary embodiment, a surgical access device that includes a first suture path extending across a working channel of the surgical access device such that one entrance of the first suture path is associated with a housing of the surgical access device and the other entrance of the first suture path is associated with a cannula that extends distally from the housing, the other entrance being located approximately on an opposed side of the device in comparison to the entrance associated with the housing. The device further includes a second suture path extending across the working channel of the surgical access device such that one entrance of the second suture path is associated with a housing of the surgical access device at a location that is approximately opposed to the entrance of the housing associated with the first suture path, and the other entrance of the second suture path being associated with the cannula at a location that is approximately opposed to the entrance of the cannula associated with the first suture path. The first and second suture paths are configured to allow an angle formed by a central axis extending through at least one of the paths and a central longitudinal axis of the surgical access device is adjustable. As a result, an angle at which a suture insertion or implant instrument that extends through the path, and thus a suture associated with such an instrument, can be adjusted to better configure the instrument and/or suture to pass through a particular thickness of tissue that is disposed adjacent to the surgical device.

The present disclosure provides a wide variety of ways by which the aforementioned angle can be adjusted with respect to one or both paths. Some non-limiting examples of such features include: multiple openings being formed in one or both of the housing and the cannula, one or more rotary discs having one or more openings of the housing formed in the disc(s); one or more elongate seals; rotary dials to control, by way of non-limiting example, an adjustable entry point that moves along an elongate length of the elongate seal(s); a slidable, floating instrument entrance that is included as part of a seal disposed within the opening(s) of the cannula to permit bite angle adjustment; a seal having a patterned guide surface that faces towards a working channel of the device and is configured to direct a surgical instrument through one or more pre-defined resealable openings of the seal; a sealing sleeve; and, in embodiments that include a sealing sleeve, a portion of the cannula having a thinner portion so that a diameter formed by the cannula and sealing sleeve is substantially similar to an outer diameter of the remainder of the cannula. A person skilled in the art, in view of the present disclosure, will understand how such features can be selectively combined and/or used independent of all other features to adjust a bite angle without departing from the spirit of the present disclosure. Further, in some embodiments, a seal (e.g., a duckbill seal) can be disposed within the working channel and can be configured to seal the working channel when no surgical instrument is disposed in the working channel. Further, the angle that is being adjusted can be adjusted between values of about 15 degrees to about 60 degrees.

In another exemplary embodiment, a surgical access device includes a housing having a central lumen that extends through it and a cannula that extends distally from the housing and is in fluid communication with the central lumen to define a working channel that is sized and configured to receive a surgical instrument. The housing further includes a sidewall disposed around the central lumen. A suture path is formed between a suture insertion entrance associated with the housing and a suture insertion exit associated with the cannula. An angle at which the path extends with respect to a central longitudinal axis extending through the cannula is selectably adjustable. More particularly, the device includes a suture path adjusting element that is configured to control the angle at which the path extends with respect to the central longitudinal axis. As a result, a user can adjust the aforementioned angle, which in turn allows a user to change the angle at which a suture disposed through the suture path enter tissue disposed proximate to the cannula.

The suture path adjusting element can have a variety of configurations based on the present disclosures. By way of two non-limiting examples, the suture path adjusting element can be a rotary dial that controls an adjustable entry port that is a suture insertion entrance disposed within an elongate opening associated with the housing, and/or one or more rotary discs of the housing having one or more openings that serve as suture insertion entrances that can be rotated to adjust the angle. In some embodiments, a second suture path can be provided. The second suture path can be controlled by the suture path adjusting element such that both paths are adjusted at the same time, or it can be independently adjustable, for instance by a second suture path adjusting element. In other embodiments the suture path adjusting element can be configured to control both suture paths independently of each other. The angle that is being adjusted can be adjusted between values of about 15 degrees to about 60 degrees.

Other features that can be incorporated in the embodiment focused on selectably adjustable suture path(s) include a slidable, floating instrument entrance that is included as part of a seal disposed within the opening(s) of the cannula to permit bite angle adjustment; a seal having a patterned guide surface that faces towards a working channel of the device and is configured to direct a surgical instrument through one or more pre-defined resealable openings of the seal; a sealing sleeve; and, in embodiments that include a sealing sleeve, a portion of the cannula having a thinner portion so that a diameter formed by the cannula and sealing sleeve is substantially similar to an outer diameter of the remainder of the cannula. A person skilled in the art, in view of the present disclosure, will understand how such features can be selectively combined and/or used independent of all other features without departing from the spirit of the present disclosure. Further, in some embodiments, a seal (e.g., a duckbill seal) can be disposed within the working channel and can be configured to seal the working channel when no surgical instrument is disposed in the working channel.

In still another exemplary embodiment, a surgical access device includes a cannula configured to be disposed in an opening in tissue, the cannula having an inner lumen extending therethrough to provide for a working channel of the surgical access device. The cannula includes a sidewall extending radially around a central longitudinal axis of the device, which can help define the inner lumen. One or more openings are formed in the sidewall such that the opening forms a passageway between the inner lumen and an outside environment. Each such opening can include a seal disposed therein. The seal can include a patterned guide surface that faces towards the inner lumen, and can be configured to direct a surgical instrument through one or more pre-defined resealable openings of the seal. The pre-defined resealable openings can also be referred to as a pre-defined rupture location. Such openings or locations can minimize or eliminate tear remnants that may result from passing an instrument through the seal, and can reduce an amount of load to be applied to an instrument being inserted through the seal to pass the instrument through the seal.

In some embodiments, the surgical access device can include some or all of the other components provided for herein, including but not limited one or more of the following features: a housing from which the cannula can extend distally, with the housing having a central lumen that extends through the housing such that the central lumen is in fluid communication with the inner lumen of the cannula to define the working channel; a seal disposed within the working channel of the surgical access device that is configured to seal the working channel when no surgical instrument is disposed through the seal; one or more openings formed in a sidewall of the housing, which in turn can define a suture path between opening(s) in the housing and opening(s) in the cannula; and one or more features configured to allow a bite angle to be adjusted. Some non-limiting examples of features configured to allow a bite angle to be adjusted are multiple openings being formed in one or both of the housing and the cannula, one or more rotary discs having one or more openings of the housing formed in the disc(s); one or more elongate seals; rotary dials to control, by way of non-limiting example, an adjustable entry point that moves along an elongate length of the elongate seal(s); a slidable, floating instrument entrance that is included as part of the patterned guide surface of the seal to permit bite angle adjustment; and a sealing sleeve that includes the patterned guide surface to help form the sealed opening of the cannula, and in some instances, a portion of the cannula has a thinner portion so that a diameter formed by the cannula and sealing sleeve is substantially similar to an outer diameter of the remainder of the cannula. A person skilled in the art, in view of the present disclosure, will understand how such features can be selectively combined and/or used independent of all other features to adjust a bite angle without departing from the spirit of the present disclosure.

BRIEF DESCRIPTION OF DRAWINGS

This disclosure will be more fully understood from the following detailed description taken in conjunction with the accompanying drawings, in which:

FIG. 5A is a perspective view of another exemplary embodiment of a surgical access device and a portion of another exemplary embodiment of a suture implant device;

DETAILED DESCRIPTION

Figure 1A:
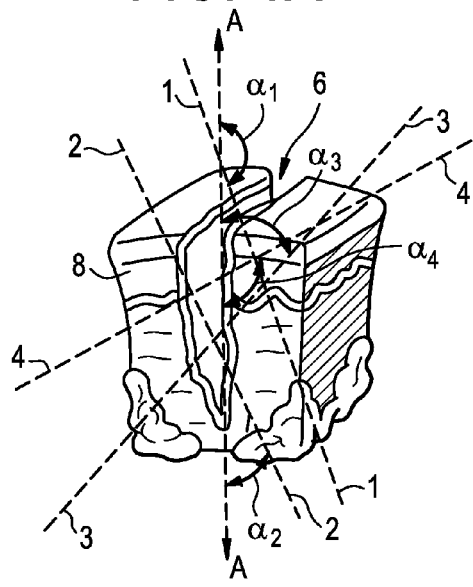
FIGS. 1A-1D are schematic illustrations of an opening formed in tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-number components of the various embodiments generally have similar features when those components are of a similar nature and/or a similar purpose. Additionally, to the extent features, sides, directions, steps, etc. are described herein as being a "first feature" or "first direction" or a "second feature" or "second direction," such numerical ordering is generally arbitrary, and thus such numbering can be interchangeable.

The terms "proximal" and "distal" are used herein with reference to a location of a clinician with respect to a surgical site, with the term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

The present disclosure generally provides for a surgical access device or system that incorporates features to improve wound (or opening) closure capabilities directly into the device or system. More particularly, the surgical access devices and systems provided for are generally described as trocars having both a housing and a cannula, with the cannula extending distally from the housing. One or more openings are associated with the housing such that an instrument, device, or suture passed through the opening also passes through the housing and into a working channel defined by the housing and the cannula. Likewise, one or more openings are associated with a sidewall of the cannula such that an instrument, device, or suture that passes through the one or more openings associated with the housing and into the working channel can be passed out of the working channel to an environment outside of the cannula via the one or more openings of the cannula sidewall. The passageway or path (sometimes referred to herein as a suture path) extending between the opening(s) associated with the housing and the opening(s) associated with the cannula can be sealed such that when no instrument, device, or suture is passed therethrough, fluid is prevented from passing between an environment outside of the surgical access device and the working channel. Suture passed through the surgical access device via the openings associated with the housing and the cannula can be passed into tissue that is proximate to the opening into which the surgical access device is disposed and subsequently cinched to close the opening while or after the surgical access device is removed from the opening.

The present disclosure also provides for a number of adjustable features that can be incorporated into the surgical access device to allow for suture that is disposed through the passageway to be passed into tissue at different angles as desired. These features include using multiple openings associated with either or both of the housing and the cannula, using components that can adjust a position of the openings with respect to a central longitudinal axis of the surgical access device, using elongate openings, rotary dials, and/or using flexible seals or sealing components, among other features. FIGS. 1A-1D provide some exemplary illustrations of potential desired stitching paths for a suture when closing an opening formed in tissue. Notably, although in each of the illustrated configurations of FIGS. 1A-1D the openings terminate and thus do not extend fully through tissue, such stitching patterns are equally applicable to openings that do extend fully through tissue, such as openings through which a trocar assembly is typically disposed.

FIG. 1A provides for one example of a potential desired stitching path for closing an opening 6 in tissue 8. As shown, there are two potential suture paths 1, 2 that extend proximally to distally from a first (as shown left) side E of a surgical access device (not shown) to a second (as shown right) side F of the surgical access device. A suture can be passed along one or both paths 1, 2. Further, one or both paths 1, 2 can be used in combination with two other paths 3, 4 also provided for that extend proximally to distally from the second side F to the first side E. As shown, the angles $\alpha_1$, $\alpha_2$, $\alpha_3$, $\alpha_4$ at which the paths are positioned with respect to a central longitudinal axis A that extends through the opening 6 (and would extend through a surgical access device when disposed through an opening), referred to herein as a bite angle, is different for different paths. This is why the ability to adjust the bite angle when the surgical access device is still disposed in the opening is desirable. By being able to adjust the bite angle defined by the locations of the opening(s) associated with the housing and cannula of the surgical access device, the different paths illustrated can be followed by sutures while the device remains in the opening. Prior to the present disclosure, these varied angles would be created by removing the surgical access device and then passing the suture through tissue at the desired angles completely independent of the surgical access device. A person skilled in the art will recognize that bite angles can be measured between any two sides of the paths and axes, and thus the illustrated configurations of the bite angles are by no means limiting to defining from where a bite angle is measured.

Figure 1B:
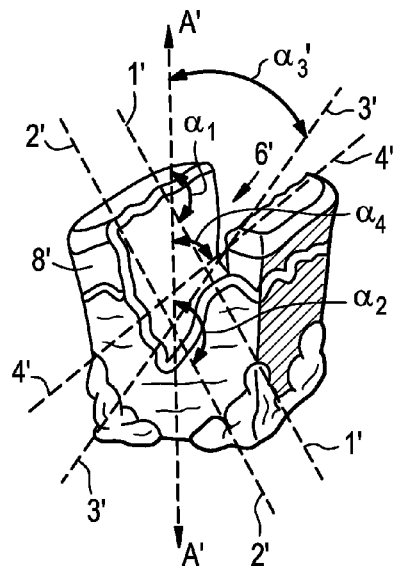
Figure 1C:
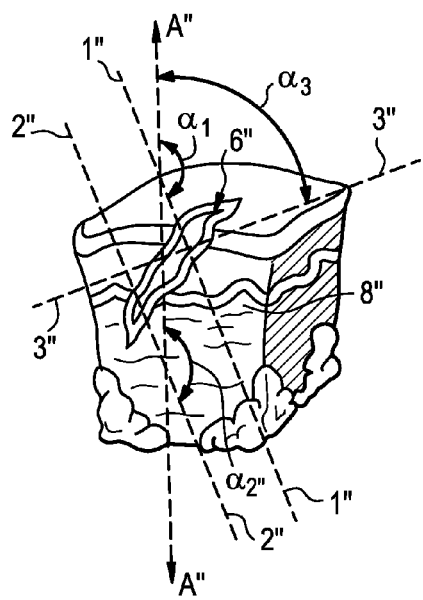
Figure 1D:
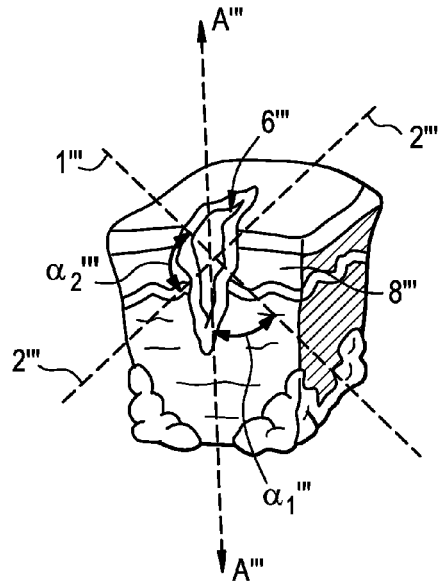

FIGS. 1B, 1C, and 1D likewise illustrated alternative path options for an opening formed in tissue. More particularly, FIG. 1B illustrates two paths 1', 2' that extend proximally to distally from a first (as shown left) side E' of a surgical access device (not shown) to a second (as shown right) side F' of the surgical access device, and two paths 3', 4' that extend from the second side F' to the first side E' to create bite angles $\alpha_1'$, $\alpha_2'$, $\alpha_3'$, $\alpha_4'$ with respect to a central longitudinal axis A' that extends through an opening 6' in tissue 8', while FIG. 1C illustrates two paths 1", 2" that extend proximally to distally from a first (as shown left) side E" of a surgical access device (not shown) to a second (as shown right) side F" of the surgical access device, and one path 3" that extends from the second side F" to the first side E". Further, FIG. 1D illustrates one path 1''' that extends from a first (as shown left) side E''' of a surgical access device (not shown) to a second (as shown right) side F''' of the surgical access device, and a single path 2''' that extends from the second side F''' to the first side E''' to create bite angles $\alpha_1''$, $\alpha_2''$, $\alpha_3''$, $\alpha_1''$ with respect to a central longitudinal axis A'' that extends through an opening 6'' in tissue 8''. In the FIG. 1D embodiment, the two paths 1''', 2''' from a perfect perpendicular angle with respect to each other, and an approximately 45 degree bite angle $\alpha_1'''$, $\alpha_2'''$ with respect to a central longitudinal axis A''' that extends through an opening 6''' in tissue 8'''. A person having skill in the art will recognize a myriad of paths that can be formed to close openings or wounds in tissue, and such paths are generally achievable in view of the disclosures provided for herein.

Trocar Assemblies

Figure 2A:
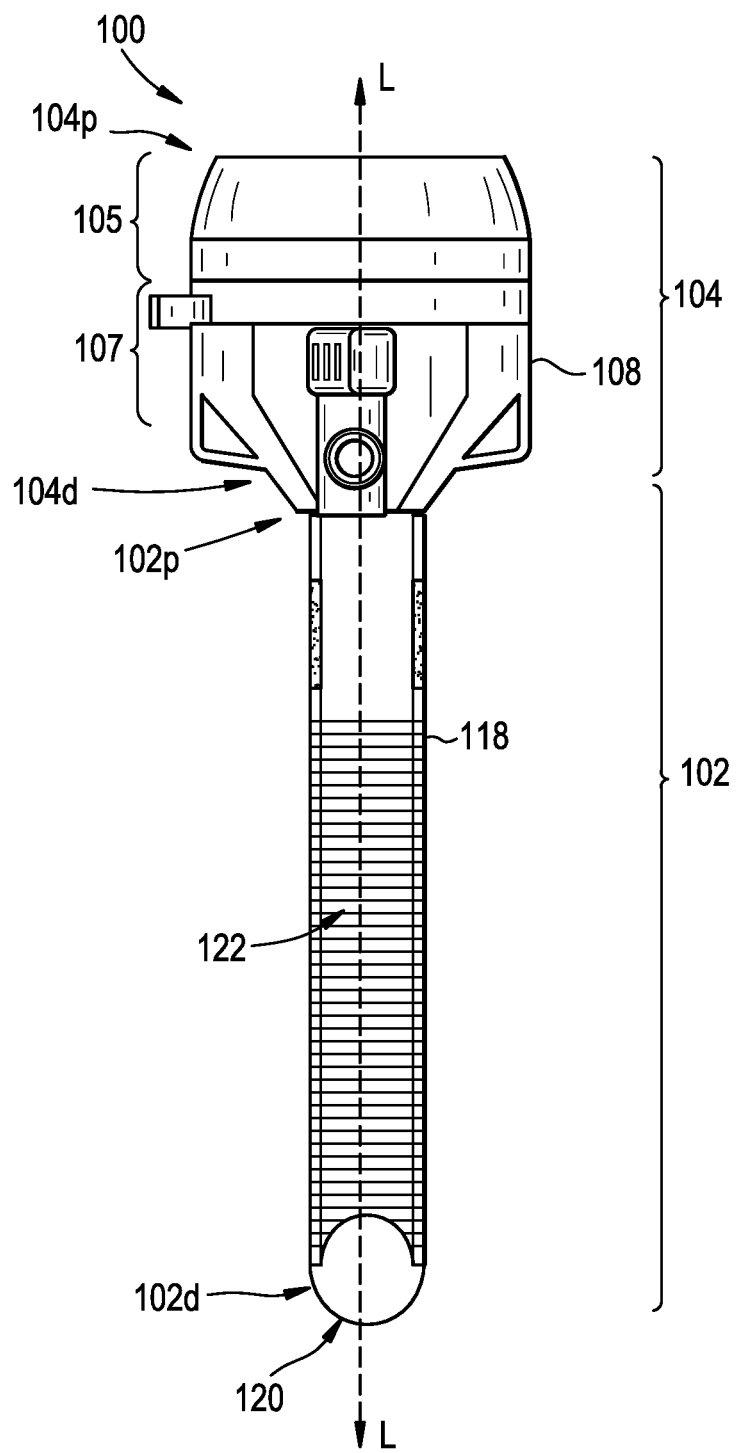
FIG. 2A is a front view of one exemplary embodiment of a surgical access device.
Figure 2B:
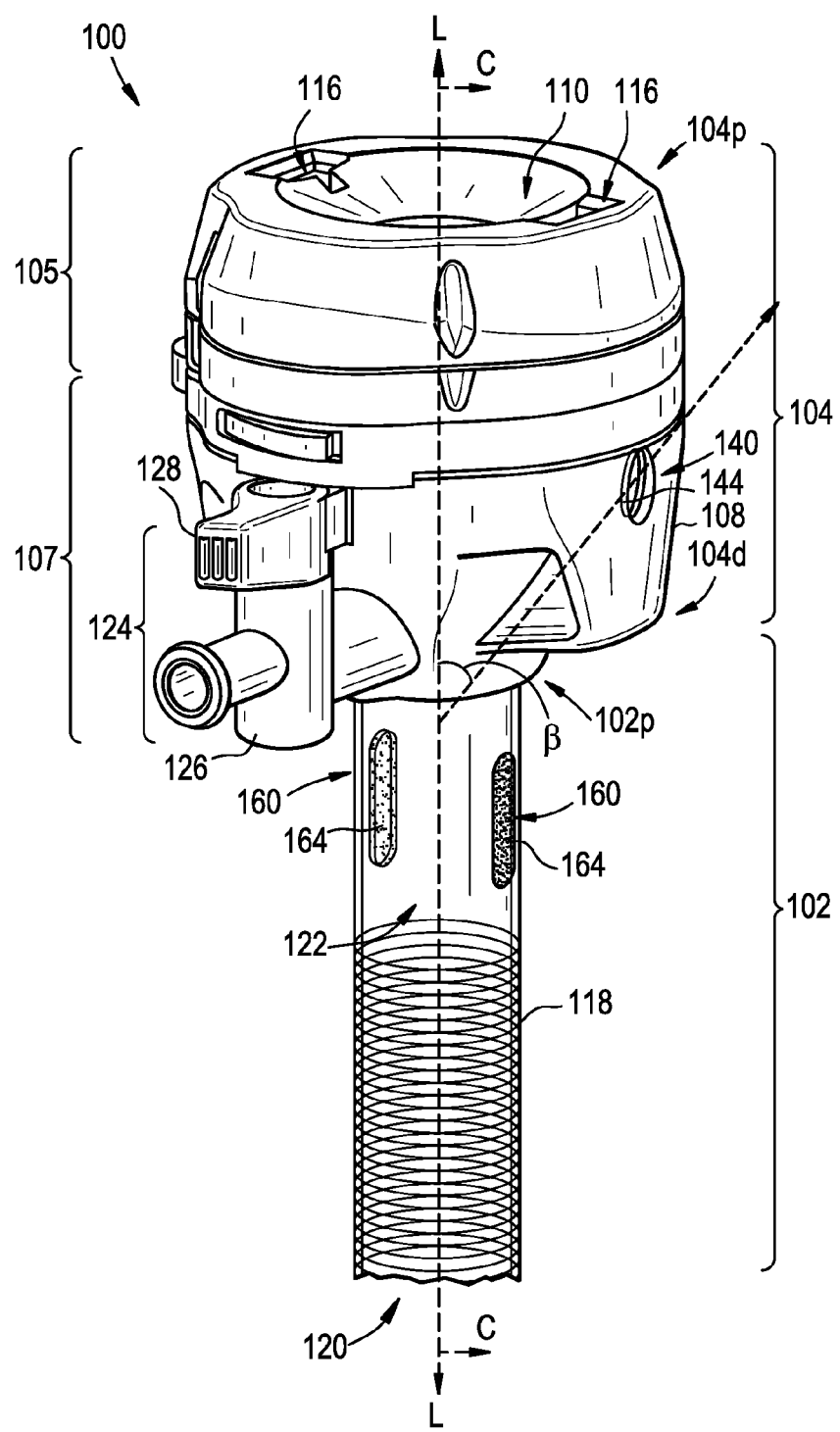
FIG. 2B is a perspective view of the surgical access device of FIG. 2A.
Figure 2C:
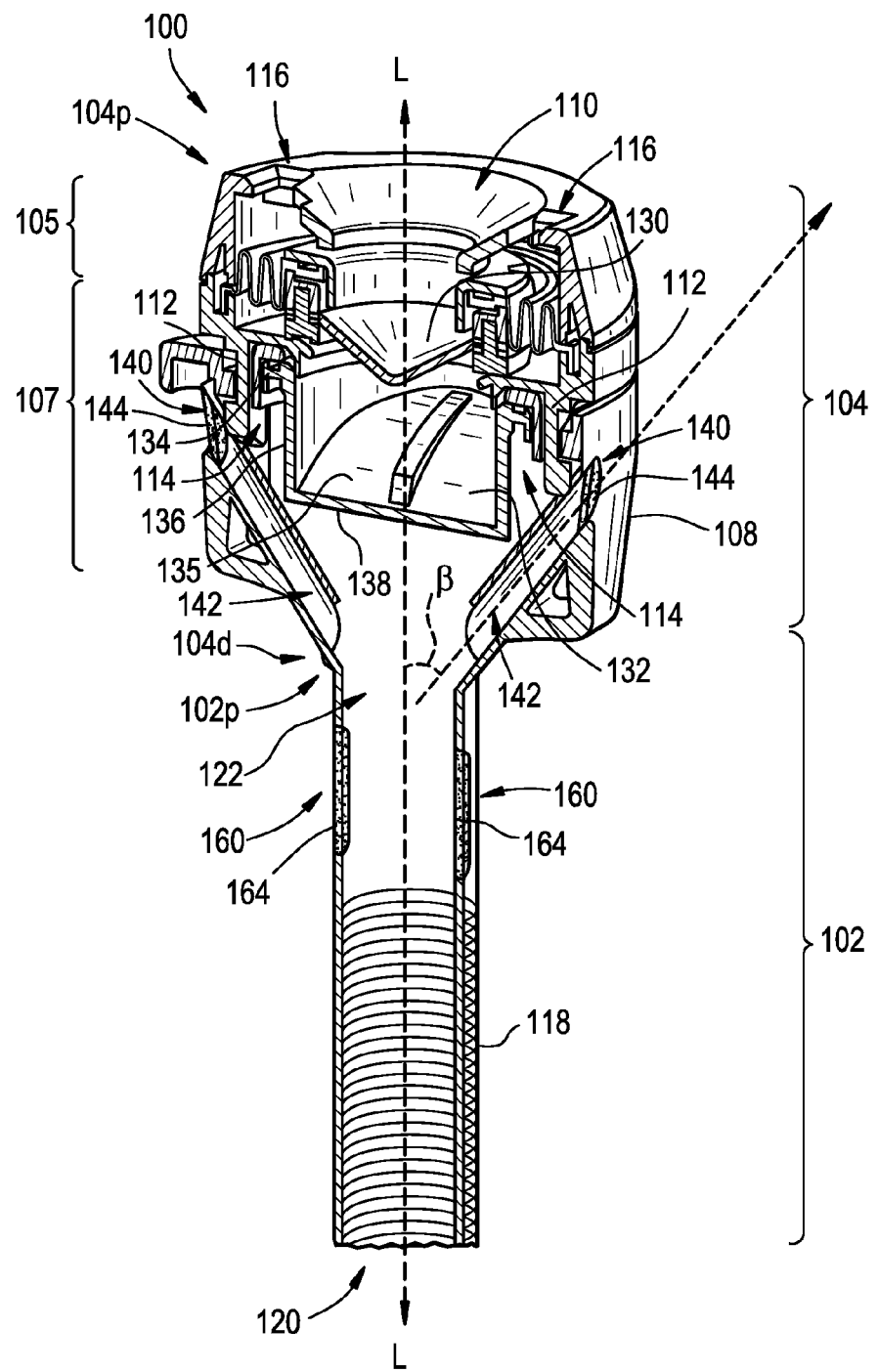
FIG. 2C is a perspective cross-sectional view of the surgical access device of FIG. 2B taken along line C-C.
Figure 2D:
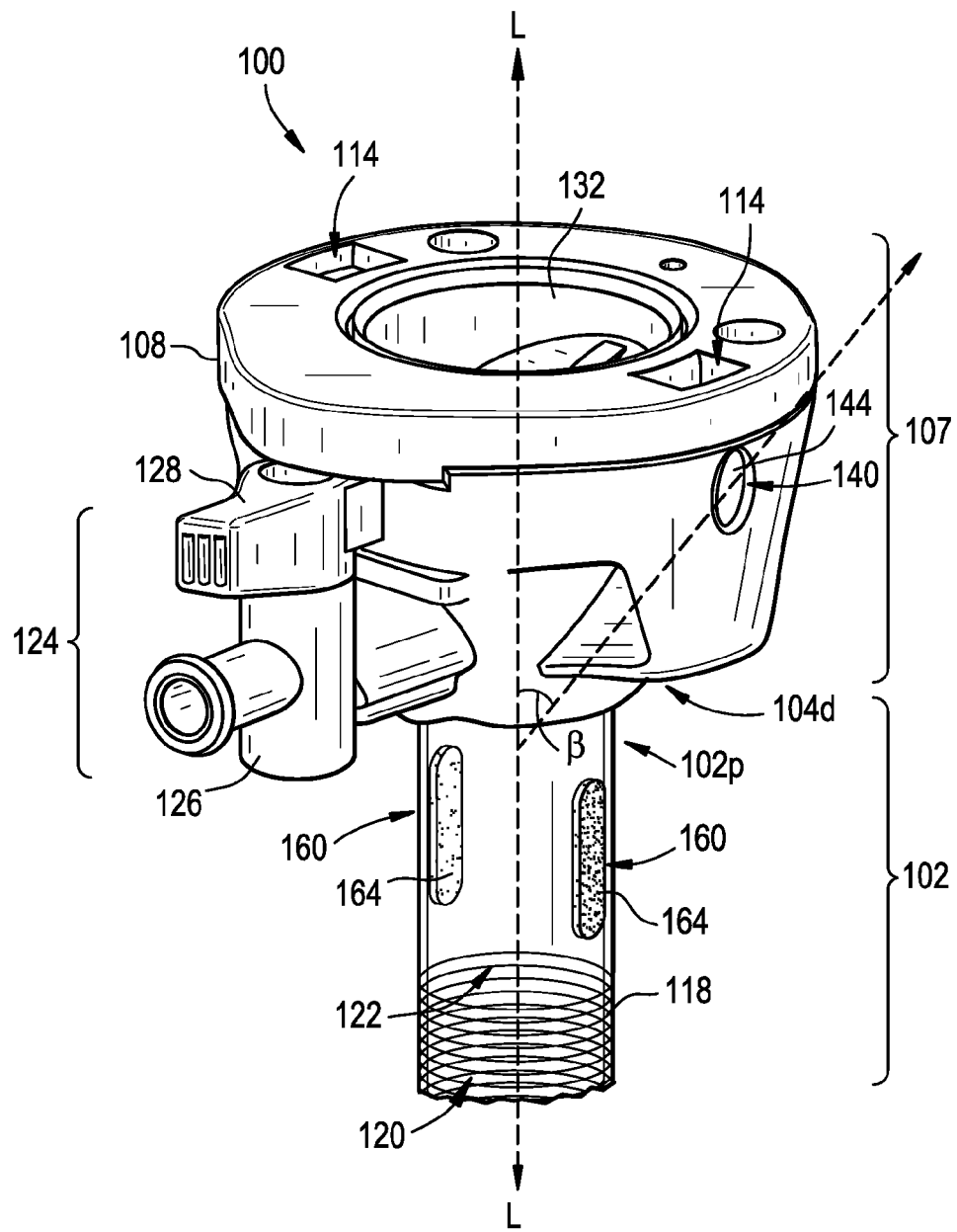
FIG. 2D is a perspective, partially transparent view of the surgical access device of FIG. 2B, with a portion of the housing removed.

FIGS. 2A-2D illustrate one exemplary embodiment of a surgical access device, as shown a trocar or trocar assembly 100. The trocar 100 can generally include a trocar cannula 102 and a trocar housing (or handle) 104. A number of configurations are available for the housing 104. In the illustrated embodiment, the housing 104 has a generally cylindrical shape having a proximal removable cap portion 105 and a distal chamber portion 107, with the cap portion 105 being selectively attachable and detachable from the distal chamber portion 107. FIG. 2D illustrates an instance in which the proximal cap portion 105 has been detached from the distal chamber portion 107. The trocar housing 104 more generally is defined by a sidewall 108 that extends circumferentially around a central longitudinal axis L extending through the trocar assembly 100, and thus the trocar cannula 102. The housing 104 includes a central lumen 110 extending from an open proximal end portion 104p to a distal end portion 104d. The housing 104 can have a variety of components disposed therein, as described below. As shown the cap portion 105 selectively mates with distal chamber portion 107 by way of male mating members, as shown tabs 112 (FIG. 2C), on the cap portion 105 engaging complementary female mating members, as shown slots 114 (FIG. 2C), formed in the distal chamber portion 107. Further, the cap portion 105 also provides for female mating members, as shown slots 116, at its proximal end for receiving various components, such as an obturator (not shown).

The trocar cannula 102 extends distally from the housing 104, and is also generally defined by a sidewall 118 that extends circumferentially around the central longitudinal axis L. A diameter of the cannula 102 is generally smaller than a diameter of the housing 104. Further, the trocar cannula 102 can define an interior lumen 120 with an open proximal end portion 102p and an open distal end portion 102d. As shown by way of FIGS. 2A and 2C, the proximal end portion 102p can extend into and be mounted in the distal end portion 104d of the trocar housing 104, thus defining a working channel 122 of the surgical access device 100 that extends from the proximal end portion 104p to the open distal end portion 102d of the cannula 102. As a result, the housing 104 is in fluid communication with the interior lumen 120 of the trocar cannula 102. Further, an insufflation port 124 can be associated with the housing 104, as shown the distal chamber portion 107, to control the flow of an insufflation fluid or gas, e.g., carbon dioxide, to a surgical site. More particularly, the insufflation port 124 can include a stop cock valve 126 and a cock valve lever 128, which can work together to allow and/or prevent passage of an insufflation fluid or gas through flexible tubing into a portion of the trocar housing 104 and the trocar cannula 102.

One or more seal assemblies can be at least partially positioned within the working channel. As shown in FIG. 2C, a first, proximal seal assembly 130 and a second, distal seal assembly 132 are both disposed in the housing and are both positioned within the working channel 122. The first, proximal seal assembly 130, also referred to as an instrument seal, is provided for in the illustrated embodiment as part of the cap portion 105. The instrument seal 130 can be adapted to cooperate with an exterior of any instrument inserted at least partially through the trocar cannula 102 such that it can sealingly engage the exterior of the instrument and thus can prevent the passage of fluids through the trocar housing 104 when the instrument is present within the trocar assembly 100. All sorts of instruments, although primarily surgical instruments, can be inserted at least partially through the trocar cannula 102. One example of such an instrument is an endoscope or a similar device that enables visualization during minimally invasive surgical procedures. One skilled in the art will recognize that many other instruments are known for insertion into at least a portion of the trocar cannula 102, and accordingly, that the proximal seal assembly 130 can likewise sealingly engage the exterior of those instruments as well.

The second, distal seal assembly 132, also referred to as a zero-closure or duckbill seal, is provided for in the illustrated embodiment as part of the chamber portion 107. The duckbill seal 132 can be configured to form a seal in the working channel 122 when no instrument is disposed therethrough to thus prevent the leakage of insufflation gases delivered through the trocar housing 104 to the body cavity. As a result, the insufflation port 124 is configured to be in fluid communication with a portion of the working channel 122 that is disposed distal of the duckbill seal 132. As shown, the duckbill seal 132 has a generally circular flange 134 with a sidewall 136 extending distally therefrom. The shape of the sidewall 136 can vary, but in the illustrated embodiment, the sidewall 136 includes opposed flaps 135 (only one is illustrated) that extend at an angle toward one another in a distal direction and that come together at a distal end to form a seal face 138. The opposed flaps 135 are movable relative to one another to allow the seal face 138 to move between a closed position, in which no instrument is disposed therethrough and the seal face 138 seals the working channel 122 of the trocar assembly 100, and an open position in which an instrument is disposed therethrough.

A person skilled in the art will recognize a variety of ways by which the seal assemblies 130, 132 can be disposed in the housing 104, as well as other locations at which one or more of the sealing assemblies can be disposed, including within the cannula 102. Further, a person skilled in the art will recognize that while in an exemplary embodiment two seal assemblies are provided in the working channel 122, in other embodiments one seal assembly, or more than two seal assemblies, can also be used in the trocar assembly 100. Still further, a person skilled in the art will recognize other components and features that can be included as part of a trocar assembly that can be included as part of the present trocar assembly 100, or other trocar assemblies, without negatively impacting the adjustability features provided for herein.

The illustrated embodiment of the trocar assembly 100, as well as other embodiments of trocar assemblies provided for herein, are exemplary, non-limiting embodiments of trocar assemblies with which the features related to wound closure can be used. A wide variety of trocar assemblies can be easily adapted in view of the present disclosures without departing from the spirit of the present disclosure. Some exemplary embodiments of trocar assemblies, and components thereof, are provided for in U.S. Pat. No. 7,981,092, U.S. Pat. No. 8,579,807, U.S. Pat. No. 8,568,362, U.S. Pat. No. 8,636,686, U.S. Pat. No. 8,690,831, U.S. Patent Application Publication No. 2015/0038793, and U.S. Patent Application Publication No. 2015/0038994, issued as U.S. Pat. No. 9,700,303 on Jul. 11, 2017, the content of each which is hereby incorporated by reference in its entirety. Further, a person having skill in the art will recognize typical materials used to form the various components of a trocar assembly, and the various sizes of trocar assemblies that can be used. By way of non-limiting examples, trocar assembly sizes with which the present disclosures can be used include $2/3$ millimeter, 5 millimeter, 8 millimeter, $10/12$, millimeter, 15 millimeter, and 18 millimeter trocar assemblies. A person skilled in the art will recognize that these trocar sizes generally delineate a size of an inner diameter of the cannula of the trocar, thus informing a user a size of an instrument that can be disposed through the cannula. An outer diameter of the trocar is thus larger. By way of non-limiting examples, an outer diameter of a 5 millimeter trocar is typically about 8.0 millimeters, and an outer diameter of a $10/12$ trocar is typically about 15.15 millimeters.

Openings or Ports Formed in Housing and Cannula

As shown best in FIGS. 2B-2D, opposed openings or ports 140 are disposed in the housing 104. The openings 140 can be formed in the sidewall 108 of the housing 104, and can extend therethrough, creating a channel 142 through which fluid can flow through. In the illustrated embodiment, the opening 140 is substantially circular and the channel 142 substantially cylindrical, although other shapes and configurations are possible without departing from the spirit of the present disclosure. A seal 144 is disposed somewhere along a length of the channel 142. In the illustrated embodiment, the seal 144 is disposed at the opening 140, which serves as a proximal entrance to the channel 142. In other embodiments, the seal 144 can be disposed further distally along a path through the channel 142, i.e., closer to the central longitudinal axis L. In the illustrated embodiment, the entrance into the channel 142 is approximately flush with the outer sidewall 108, and the channel 142 that extends into the working channel 122 is disposed at an oblique angle β with respect to the central longitudinal axis L such that the channel terminates distal of the distal-most seal, i.e., the duckbill seal 132, thereby forming a suture path between an outside environment and a surgical site. The present configuration allows insufflation to be substantially maintained even as an instrument or suture is passed through the channel 142. As shown, the proximal end of the channel 142 is disposed approximately in the same horizontal plane as a portion of the distal-most seal 132, but it does not have to be so disposed. The openings 140 promote fluid communication between an outside environment and the working channel when the seal 144 associated with the channel 142 is open.

FIGS. 2A-2D illustrate opposed openings or ports 160 disposed in the cannula 102 as well. The openings 160 can be formed, and extend through, the sidewall 118 of the cannula 102. A seal 164 is associated with the opening 160, for instance by sitting within the opening 160, or as described in later embodiments, by having a sleeve that serves as a seal disposed around the cannula at the opening. In some instances, the openings 160 can be referred to as sealed openings or ports because of the proximity of the seal 164 with respect to the opening 160. The openings 160 formed in the cannula 102 are accessible by an instrument, device, or suture that is passed through the housing opening 140 and through the working channel 122. Thus, a plurality of paths can be formed between the opening(s) 140 of the housing 104 and the opening(s) 160 of the cannula 102, the paths passing across the working channel 122 of the device 100. The sealed openings or ports 160 can have a variety of shapes and configurations, but in the illustrated embodiment both openings 160 are elongate, having a substantially elliptical shape. The elongate nature of the ports 160 allows for different bite angles to be achieved, and can be used in conjunction with other adjustability features and particularly configured seals to achieve desired results as described herein. The inclusion of openings or ports 140, 160 in association with both the housing 104 and the cannula 102 is one particularly useful and independently novel aspect of the present disclosure. Another separate, but also particularly useful and independently novel aspect of the present disclosure, is the ability for bite angles to be adjusted across one or more suture paths that are formed through a surgical access device like the trocar assembly 100.

The materials used to form the seals 164, as well as the seals 144 associated with the housing 104, can be any materials known to those skilled in the art, including but not limited to various elastomers and rubbers, such as polyisoprene, Butyl rubber, anionically polymerized isoprene (e.g., Kraton® as manufactured by Kraton Polymers of Houston, Tex.), polyurethane, silicone, and other similar materials. Some seals can be manufactured from more than one of these materials. In the illustrated embodiment, the openings 140 formed in the housing 104 and the openings 160 formed in the cannula 102 are substantially aligned such that longitudinally extending planes that pass through an approximate entirety of the respective openings 160 are substantially parallel to longitudinally extending planes that extend through an approximate entirety of the respective openings 140 in the housing 104. However, the openings 140, 160 can generally be disposed at any location around the circumference of the respective housing 104 and cannula 102 as desired, and as described below, their locations can be manipulated.

Suture Insertion Devices and Use of the Same with Trocar Assemblies

Figure 3:
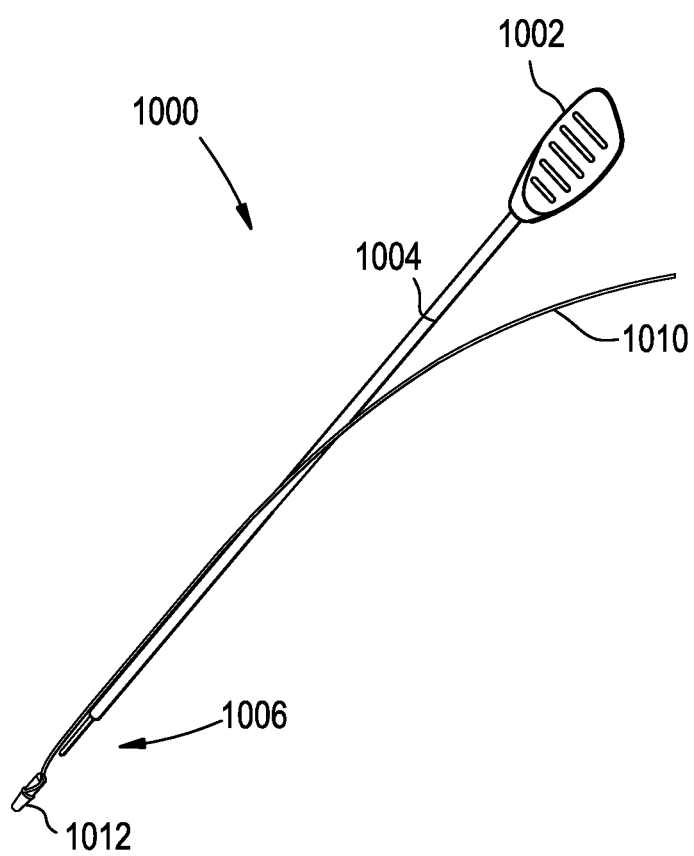
FIG. 3 is a perspective view of one exemplary embodiment of a suture implant device having a suture associated therewith.

FIG. 3 provides for one exemplary embodiment of a suture insertion device 1000, also referred to as a suture implant device, that can be used in conjunction with the surgical access devices provided for herein. Such devices are known to those skilled in the art, and thus a detailed explanation as to how they work is unnecessary. Generally, the device 1000 includes a proximal handle or gripping portion 1002, an elongate shaft 1004 extending from the proximal handle portion 1002, and a distal tip or needle 1006 that is configured to puncture tissue and/or hold a suture at a position relative to the device 1000 to aid in passing the suture into and through a surgical access device and then into tissue disposed proximate to that surgical access device. In the illustrated embodiment, a suture 1010 is coupled to a connecting anchor or member 1012, and the connecting anchor 1012 is coupled to the distal tip 1006 of the device 1000 to secure the suture relative to the device. More particularly, the connecting anchor 1012 has a lumen (not shown) extending through a portion thereof, and the distal tip 1006 of the device 1000 and inner walls of the anchor 1012 surrounding the lumen of the anchor 1012 are configured to be removably coupled together. Other mechanisms and manners for connecting the suture 1010 to the device 1000 are possible. By way of non-limiting example, a spring-biased stylet having a tip needle can be used, such as an Endo Close™ insertion device, as manufactured by Medtronic of Dublin, Republic of Ireland. Further, as described below, the connecting anchor 1012 can be disconnected from the suture insertion device 1000 and subsequently coupled with a second connecting anchor to form a single suture.

One exemplary embodiment of using the suture insertion device 1000 with the surgical access device 100 is illustrated in FIGS. 4A-4E. As shown, the suture insertion device 1000 can be passed through the opening 140 (identified for purposes of FIGS. 4A-4E as 140a to distinguish it from the opposed opening 140, which is identified for purposes of FIGS. 4A-4E as 140b) in the housing 104, through the working channel 122, and through the sealed opening 160 (identified for purposes of FIGS. 4A-4E as 160b to distinguish it from the opposed opening 160, which is identified for purposes of FIGS. 4A-4E as 160a) in the cannula 102 that is opposed to the opening 140a so that the connecting anchor 1012 and at least a portion of the suture insertion device 1000 is disposed outside of the surgical access device 100, proximate to tissue in which the surgical access device 100 is disposed. The suture 1010 can be coupled to the suture insertion device 1000, for instance by way of the connecting anchor 1012, and upon exiting the opening 160b, can be passed through tissue proximate to an opening in which the surgical access device 100 is disposed for future closure of the opening. The connecting anchor 1012, and thus the suture 1010, can be disconnected from the suture insertion device, and the suture insertion device removed, thereby leaving the suture 1010 and connecting anchor 1012 in the configuration illustrated in FIG. 4B.

The suture insertion device 1000, or another suture insertion device, can also be operated to pass a second suture 1010' into and through the surgical access device 100. For example, the device 1000 can be passed into the other housing opening 140b, through the working channel 122, and through the other sealed opening 160a so that a connecting anchor or member 1012' associated with the second suture 1010' and at least a portion of the suture insertion device 1000 is disposed outside of the surgical access device 100, proximate to tissue in which the surgical access device 100 is disposed. Subsequent removal of the suture insertion device 1000 can result in the configuration illustrated in FIG. 4C.

Figure 4A:
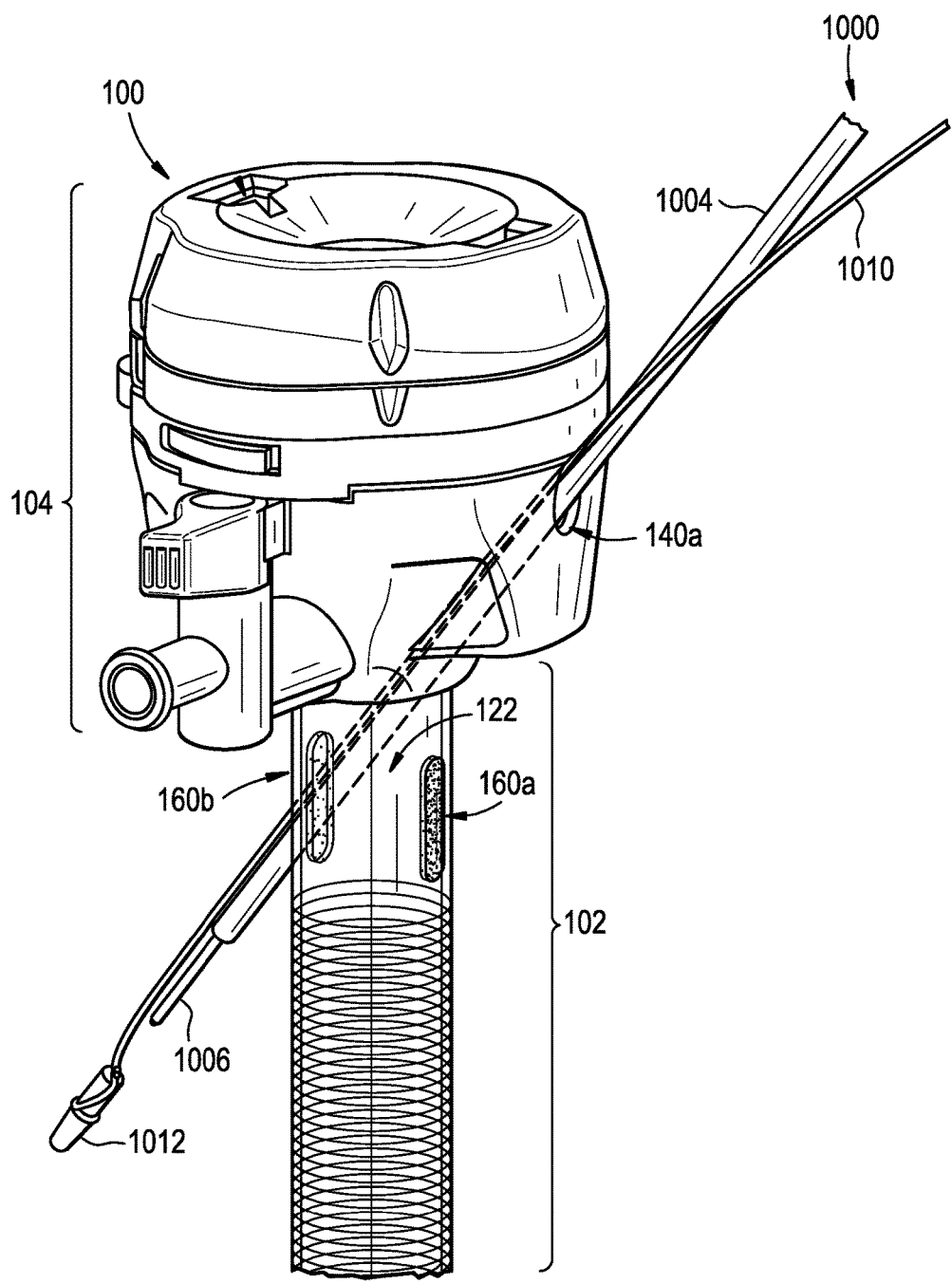
FIG. 4A is a perspective, partially transparent view of the surgical access device of FIG. 2A having the suture implant device and suture of FIG. 3 disposed therethrough.
Figure 4B:
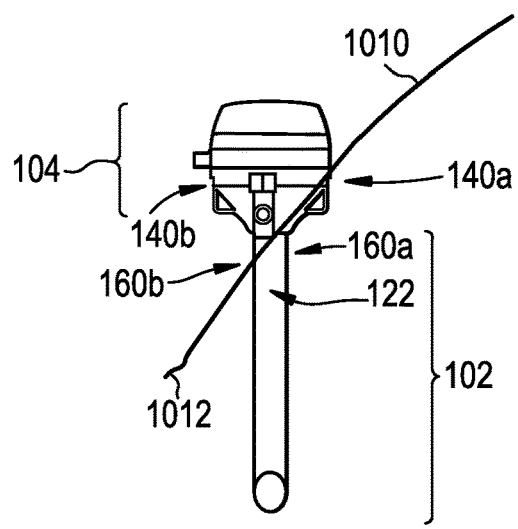
FIG. 4B is a front view of the surgical access device of FIG. 4A with the suture implant device removed from the surgical access device.
Figure 4C:
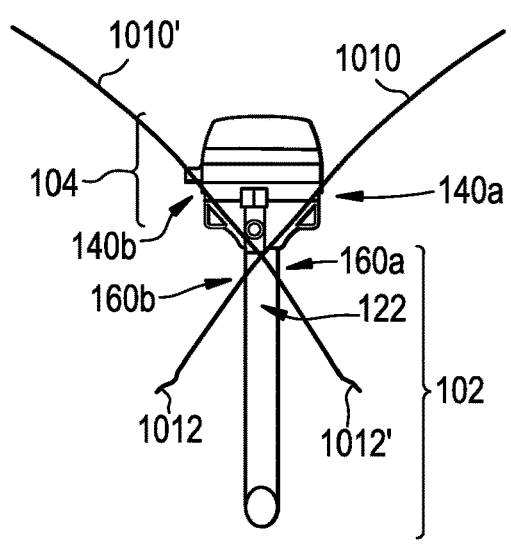
FIG. 4C is a front view of the surgical access device of FIG. 4B with a second suture disposed therethrough.
Figure 4D:
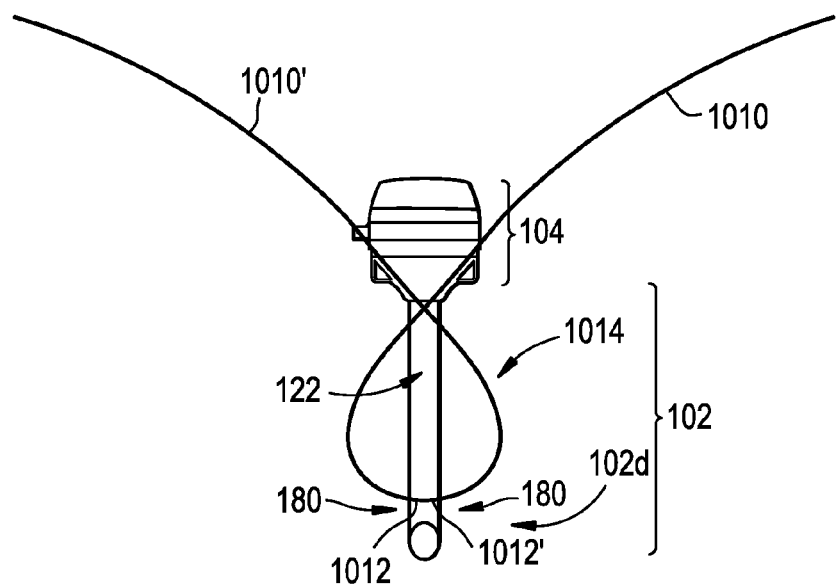
FIG. 4D is a front view of the surgical access device of FIG. 4C having the first and second sutures coupled together to form a loop.
Figure 4E:
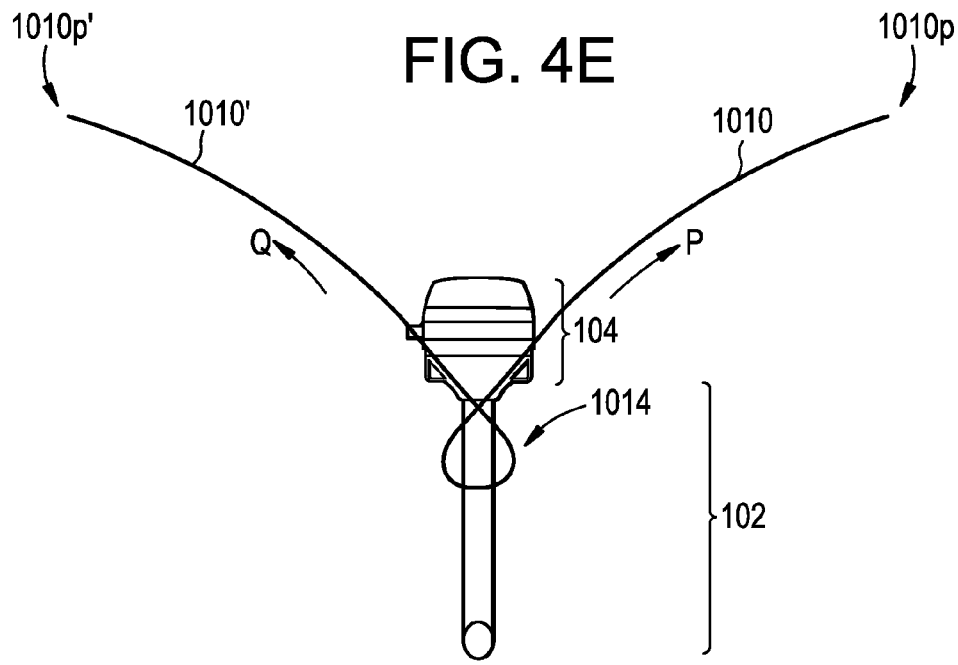
FIG. 4E is a front view of the surgical access device of FIG. 4D illustrating the loop being collapsed.

As shown in FIG. 4D, the two connecting members 1012, 1012' can be coupled together so that the first and second sutures 1010, 1010' form a single suture loop 1014. In the illustrated embodiment, the members 1012, 1012' are passed through sealed openings 180 located at a distal end 102d of the cannula 102. The sealed openings 180 can have at least some of the same characteristics described above with respect to the sealed openings 160a, 106b, thus preventing fluid from unnecessarily passing between the working channel 122 and the outside environment. In other embodiments, the connecting members 1012, 1012' can be coupled outside of the surgical access device 100, or alternatively, the two sutures 1010, 1010', and/or additional sutures passed through openings 140, 160 of the surgical access device 100, can be operated independently to close the opening through which the surgical access device 100 is disposed. Turning back to the illustrated embodiment, the formed loop 1014 can then be closed, for instance by applying tension in direction P and Q to proximal ends 1010p, 1010p' of one or both sutures 1010, 1010', respectively, as shown in FIG. 4E. The tension can be applied as the surgical access device 100 is being removed from the opening in tissue, or after it has been removed, to quickly and efficiently close the opening through which the surgical access device 100 was disposed.

Alternative Embodiment of Surgical Access Device and Suture Insertion Device

FIGS. 5A-5E illustrate another exemplary embodiment of a surgical access device, as shown a trocar assembly 200, as well as another exemplary embodiment of a suture insertion device 2000. The trocar 200 generally includes a trocar cannula 202 and a trocar housing (or handle) 204, and has similar features and components as the trocar assembly 100. Accordingly, it is unnecessary to discuss in any detail components such as a removable cap portion 205, distal chamber portion 207, central lumen 210, interior lumen 220, working channel 222 formed by the central and interior lumens 210, 220, insufflation port 224, and seals (not shown), among other components. The construction and operation of such components are understood by a person skilled in the art in view of the disclosures provided for herein related to such components amongst the various provided for embodiments.

One illustrated difference between the trocar 100 and the trocar 200 is the location of the openings or ports 240 that are associated with the housing 204. While the openings or ports 240 of the trocar 200 include channels 242 that extend between an outside environment and the working channel 222, and seals 244 (FIG. 5C) associated therewith, an entrance of the channel 242 in FIGS. 5A-5E is not flush with respect to a sidewall 208 of the housing 204. As shown, the opposed channels 242 extend separate from the sidewall 208, and entrances of the channels 242 are further away radially from a central longitudinal axis L' of the device 200 than the outer sidewall 208 is located. Further, as illustrated in FIG. 5E, the entrances are angled with respect to the central longitudinal axis L'. More particularly, as shown, an angle γ formed by a plane J that extends substantially across the entrance of the channel 242 and the central longitudinal axis L' is oblique. The channel 242 still communicates with the working channel 222 and an opposed sealed opening 260 formed in a sidewall 218 of the cannula 202 as provided for with respect to the sealed opening 160 of the trocar 100, as shown in FIGS. 5C and 5E. Further, the path formed by the opposed openings 240 and 260 is sealed at both ends, for example by providing for a seal 244 proximate to the entrance of the channel 242 and a seal 264 associated with the opening 260 extending through the cannula 202. In the illustrated embodiment, the sealed openings 260 of the cannula 202 are formed by openings (not shown) formed in the sidewall 218 and a sleeve 270 disposed around the cannula 202, the sleeve 270 having pre-formed seals 264 formed therein that are complementary in shape to the openings 260 such that the combination of the openings 260 and the seals 264 form sealed openings of the cannula 202. As shown, the sleeve 270 increases a diameter of the cannula 202, but in other embodiments, as described below for instance with respect to FIGS. 23-25, the cannula and/or sleeve can be configured such that the diameter of the combination of the cannula and the sleeve is approximately equal to the diameter of the cannula at locations where the sleeve is not disposed.

Figure 5B:
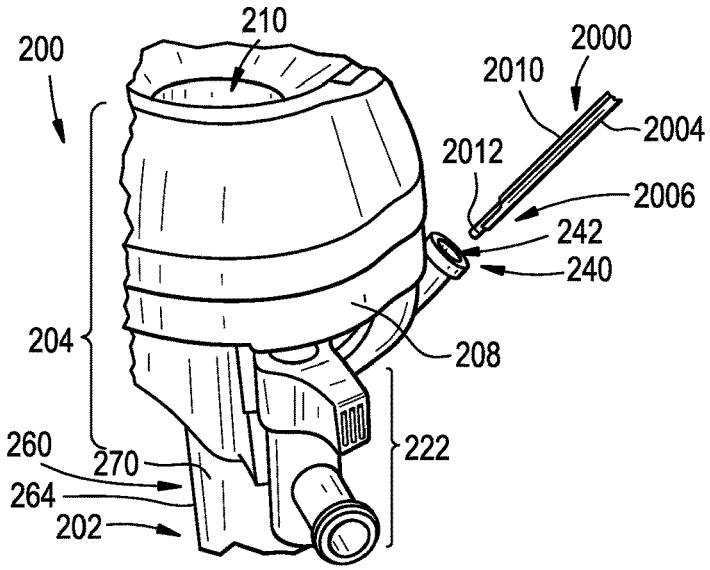
FIG. 5B is a detailed perspective view of the surgical access device and a portion of the suture implant device of FIG. 5A.
Figure 5C:
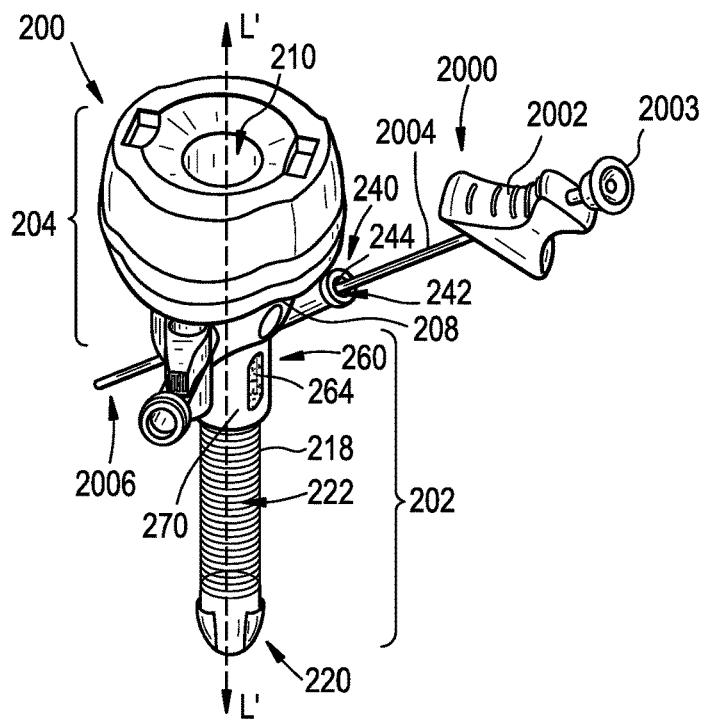
FIG. 5C is a perspective view of the surgical access device and the entire suture implant device of FIG. 5A with the suture implant device being disposed through the surgical access device.
Figure 5D:
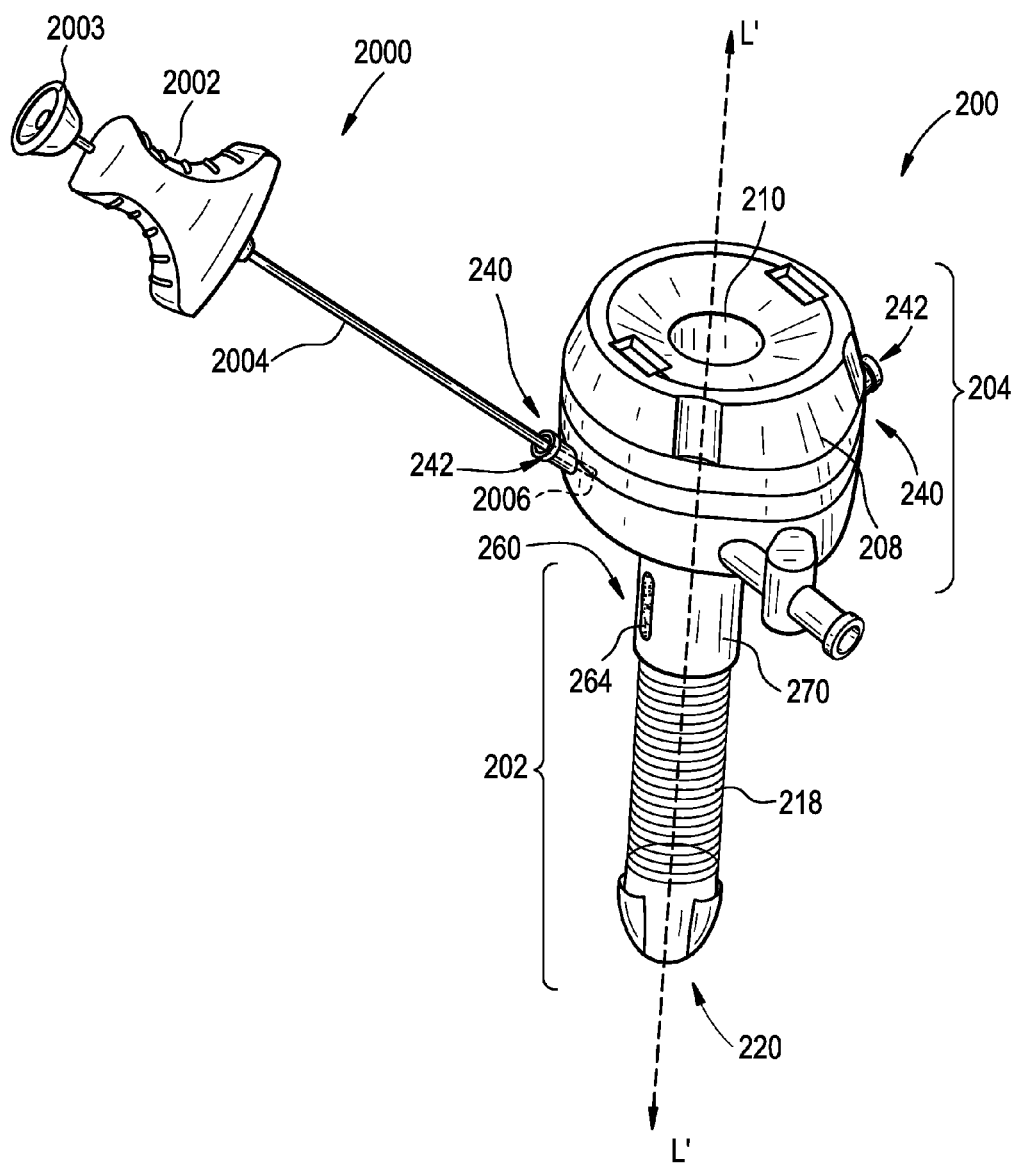
FIG. 5D is a perspective view of the surgical access device and suture implant device of FIG. 5C with the suture implant device being removed from the surgical access device and located adjacent to an opposite side of the surgical access device.
Figure 5E:
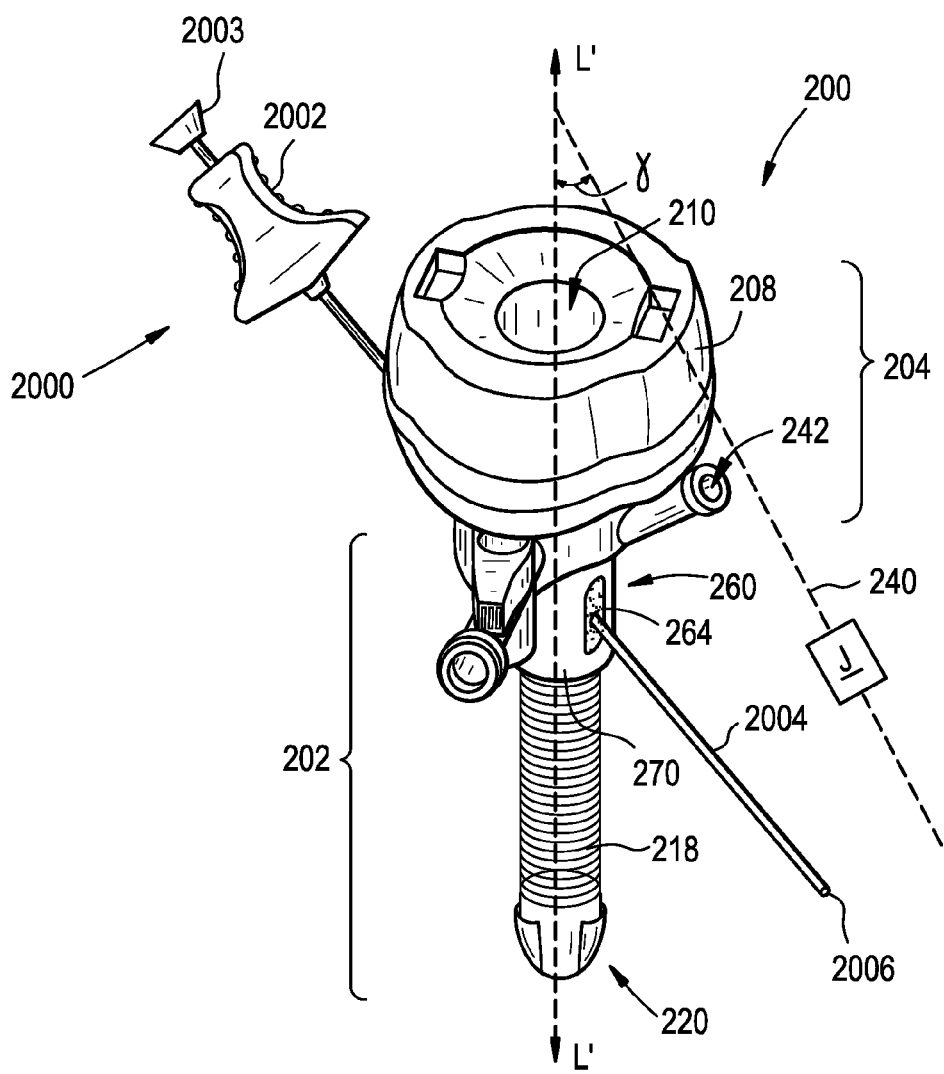
FIG. 5E is a perspective view of the surgical access device and suture implant device of FIG. 5D with the suture implant device disposed through the surgical access device.

Further, the suture insertion or implant device 2000 provided for in FIGS. 5A-5E is an alternative arrangement of a suture insertion device. The device 2000 generally includes a proximal handle portion 2002, an elongate shaft 2004, and a distal tip or needle 2006, all of which are similarly constructed as the suture insertion device 1000. One illustrated difference is that the proximal handle portion 2002 includes a spring-loaded actuator 2003, which is spring-biased into a retaining position to maintain a location of a suture 2010 (FIG. 5B) with respect to the device 2000. Pressing the actuator 2003 can release the suture 2010 from the device 2000, thus allowing the device 2000 to be removed and the suture 2010 used to complete the surgical repair. In some embodiments, a connecting anchor or member 2012 can be used to assist in associating the suture 2010 with the device 2000, as shown in FIG. 5B.

In use, the suture insertion device 2000 having the suture 2010 associated therewith is passed from an outside environment, into the opening 240 through the entrance into the channel 242, through the working channel 222, and out of the sealed opening 260 to the surgical site. The suture 2010 is decoupled from the insertion device 2000 and the insertion device 2000 is removed. The suture insertion device 2000 then has a second suture associated therewith (or, alternatively, a second suture insertion device is used in conjunction with a second suture), is passed from an outside environment, into the opposed opening 240 through the entrance into the opposed channel 242, through the working channel 222, and out of the other sealed opening 260 to the surgical site. The suture is again decoupled from the insertion device 2000 (or second suture insertion device) and the insertion device 2000 removed. The sutures can then be operated to close the opening through which the trocar 200 is disposed as or after the trocar 200 is removed from the opening.

Surgical Access Devices with Multiple Openings Proximate to Each Other

Figure 6:
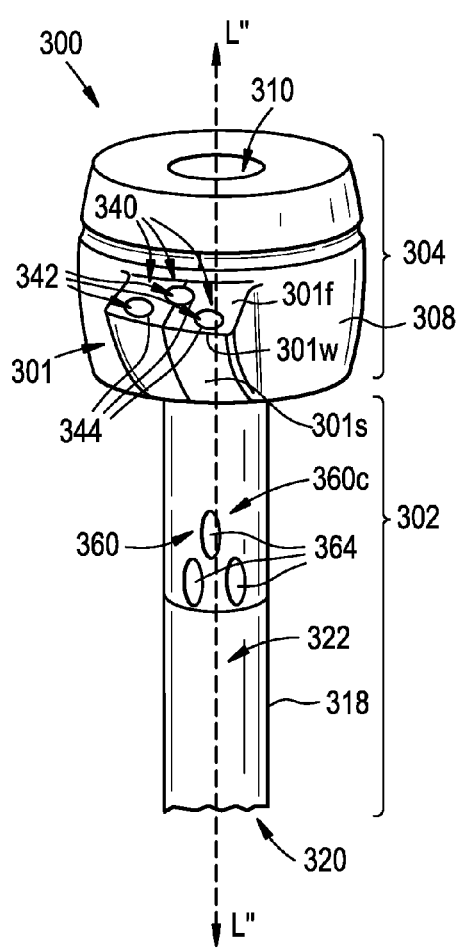
FIG. 6 is a perspective view of yet another exemplary embodiment of a surgical access device, the device having multiple ports associated with each of a housing and a cannula of the surgical access device.
Figure 7:
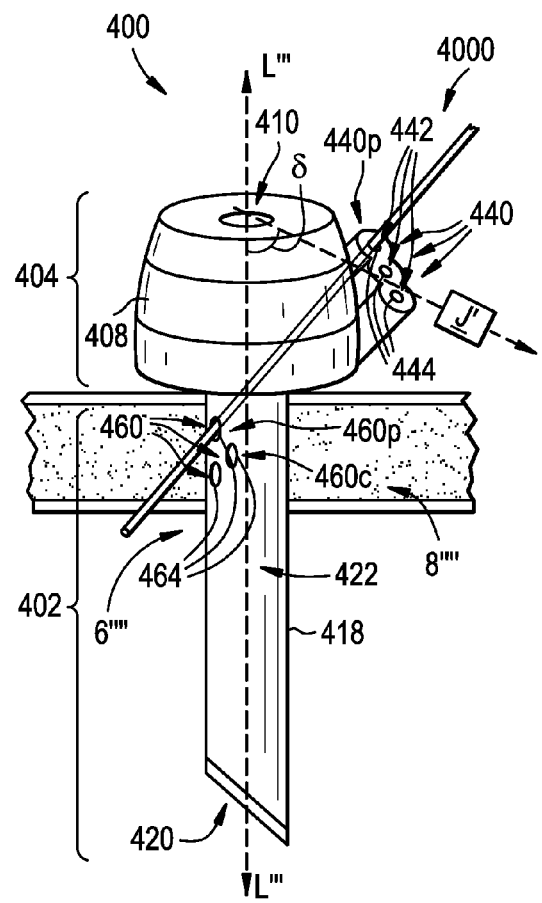
FIG. 7 is a perspective view of another exemplary embodiment of a surgical access device having multiple ports associated with each of a housing and a cannula of the device, as well as a portion of a suture implant device disposed through the surgical access device.

FIGS. 6 and 7 provide two alternative embodiments of surgical access devices having multiple openings associated with each of a housing and a cannula, with the openings in each of the housing and cannula being proximate to each other. In other words, while previous embodiments included multiple openings formed in a housing and multiple openings formed in a cannula, those openings were generally opposed to each other so that one opening in a housing and one opening on an opposed side of the cannula formed a suture path. There were not multiple openings formed on the same side of a housing or a cannula to provide various suture path options having forming different bite angles. The embodiments of FIGS. 6 and 7, however, provide multiple openings in the same component that are proximate to each other, which provides the ability for different bite angles to be achieved depending on through which openings a suture insertion device and/or a suture are passed.

As shown in FIG. 6, a trocar 300 having both a housing 304 and a cannula 302 extending distally therefrom includes a port extension 301 extending radially from the otherwise cylindrically-shaped housing 304. The extension 301 includes a plurality of openings or ports 340 formed therein, each port or opening serving as an entrance to a channel 342 that extends through the extension 301, through the housing 304, and into a working channel 322 extending through the trocar 300. As with other embodiments, the working channel 322 is formed by a central lumen 310 extending through the housing 304 and an interior lumen 320 extending through the cannula 302. Each opening 340 can have a seal 344 associated therewith, either at the entrance or further in the channel 342, between the entrance and the working channel 322. The openings 340 can be formed in any pattern, but in the illustrated embodiment there are three openings 340 having a triangular pattern formed between the three openings. The extension 301 can be any size and shape, depending, at least in part, on the desired bite angle, the number of desired openings 340, and the components and methods with which the trocar 300 is designed to be used. In the illustrated embodiment, the extension 301 has a substantially pyramidal shape with the openings 340 being formed in a substantially flat, proximal-facing surface 301f, and an angled side 301s that extends radially from the sidewall 308 to lead to an outer-most wall 301w of the substantially flat, proximal-facing surface 301f. Although not illustrated, a complimentary extension, along with one or more openings or ports, can be formed on an opposed side of the device 300, or at any other location along a circumference of the housing 304.

Multiple openings or ports 360 can also be formed in a sidewall 318 of the cannula 302, with the multiple openings 360 being proximate to each other. Similar to the openings 340 of the housing 304, the openings 360 can be formed in any pattern, but in the illustrated embodiment there are three openings 360 having a triangular pattern formed between the three openings 360, with one opening, a central vertex 360c (i.e., the opening that is approximately equidistantly spaced from the other two openings), being more proximal than the other two, which are substantially aligned with respect to a longitudinal axis L" extending through the device 300. Each of the openings 360 can be sealed in manners similar to those described elsewhere herein as it pertains to openings or ports associated with the cannula, and thus in some embodiments can include a seal 364 disposed within each opening 360. Additionally, although not illustrated, openings 360 of the nature illustrated with respect to FIG. 6 can also be formed on an opposed side of the cannula 302, or at any other location along its circumference. Further, any one of the openings 360 formed in the cannula 302 can be used in conjunction with any one of the openings 340 formed in the extension 301. Each different combination of openings 340, 360 in the housing 304 and cannula 302 can provide for a different bite angle.

FIG. 7 provides for another configuration of a trocar 400 having multiple openings 440, 460 proximate to each other in both a housing 404 and a cannula 402 extending distally from the housing 404, respectively, to allow for multiple bite angles. In the illustrated embodiment, the trocar 400 is disposed in an opening 6"" formed in tissue 8"". The openings or ports 440 associated with the housing 404 of the illustrated embodiment are configured in a manner similar to the openings 240 of the trocar 200 of FIGS. 5A-5E, and can be used in conjunction with the openings 460 to pass a suture along a path extending therebetween and into tissue to close the opening 6"" as or shortly after the trocar 400 is removed from the opening 6"".

As shown, three openings or ports 440 extend radially from a sidewall 408 of the housing 404, with each port 440 being more distal than an adjacent port. In the illustrated embodiment, the three ports 440 are substantially aligned along a longitudinal axis M that is substantially parallel to a central longitudinal axis L''' of the device 400. In other embodiments, one or more of the ports 440 can be located in a position that is at a location other than substantially longitudinally aligned with one or more of the other ports 440. Each port 440 can include a channel 442 that extends from an outside environment, through the housing 404 and into a working channel 422 extending through the device that is defined by a central lumen 410 of the housing and an inner lumen 420 of the cannula 402. In the illustrated embodiment, an entrance of each channel 442 is disposed radially further away from the central longitudinal axis L''' than the sidewall 408 is located with respect to the central longitudinal axis L'''. Each channel 442 includes a seal 444 associated therewith, either at the entrance or disposed further distally along the channel 442 so that the outside environment is sealed from the working channel 422. A plane J' extending substantially through the entrance of the channel 442 can form an oblique angle δ with respect to the central longitudinal axis L'''.

Multiple openings or ports 460 can also be formed in a sidewall 418 of the cannula 402, with the multiple openings 460 being proximate to each other. Similar to the openings 440 of the housing 404, the openings 460 can be formed in any pattern, but in the illustrated embodiment there are three openings 460 having a triangular pattern formed between the three openings, with one opening, a central vertex 460c (i.e., the opening that is approximately equidistantly spaced from the other two openings), being disposed to the right of the other two co-aligned vertices as shown. One of the two c-aligned vertices, a proximal-most vertex 460p, is more proximal than the other two vertices. Each of the openings 460 can be sealed in manners similar to those described elsewhere herein as it pertains to openings or ports form in the cannula, and thus in some embodiments can include a seal 464 disposed within each opening 460. Additionally, although not illustrated, openings 460 of the nature illustrated with respect to FIG. 7 can also be formed on an opposed side of the cannula 402, or at any other location along its circumference. Further, any one of the openings 460 formed in the cannula 402 can be used in conjunction with any one of the openings 440 extending from the housing 404. Each different combination of openings 440, 460 in the housing 404 and cannula 402 can provide for a different bite angle. Further, in some embodiments, either or both of the openings associated with the housing 404 and the openings 460 associated with the cannula 402 can be labeled to help users identify the bite angles that are achieved. The markings can be formed on the sidewalls 408 and 418 at locations visible to a user and/or visible using an endoscope or other viewing instrument to view the markings.

In the illustrated embodiment, a suture insertion or implant device 4000 is illustrated passing through a proximal-most opening 440p of the housing openings 440 and the proximal-most opening 460p of the cannula openings 460. While the location of an opening 440 in the housing 404 through which a suture insertion device can be similar to the location of an opening 460 in cannula through which the same device is inserted, i.e., the device passing through the proximal-most openings of both the housing and cannula, a suture insertion device and/or suture can be passed from any of the openings of the housing to any of the openings of the cannula. Accordingly, a first position can be in which a device and/or suture passes through the proximal-most housing opening and the proximal-most cannula opening, a second position can be in which a device and/or suture passes through the proximal-most housing opening and one of the distal-most cannula openings, a third position can be in which a device and/or suture passes through the proximal-most housing opening and the other of the distal-most cannula openings, a fourth position can be in which a device and/or suture passes through the middle housing opening and the proximal-most cannula opening, and so forth. Any number of positions can be achieved depending, at least in part, on the number of openings provided in the housing and cannula, the adjustability of those openings (as described below), and the size and shape of the openings and instruments used in conjunction therewith. In use, a person skilled in the art, in view of the present disclosures, will recognize how to select different openings to pass an insertion instrument and/or suture through to achieve desired bite angles. The various bite angles can be used to pass suture into the tissue 8'''' in various configurations to allow the opening 6'''' to be closed while or shortly after the trocar 400 is removed from the opening 6''''. A person skilled in the art will recognize that while some other surgical access device embodiments provided for herein are not illustrated with respect to a tissue or an opening or wound formed in the tissue, the other embodiments can be used to close openings in which the surgical access device is disposed while or shortly after the device is removed from such an opening or wound in view of the present disclosures.

Surgical Access Device Having Elongate, Adjustable Openings

FIGS. 8-11 illustrate one exemplary embodiment of a surgical access device, e.g., a trocar 500, having an elongate opening or slot 540 formed in a housing 504 of the device 500, with the elongate opening 540 including an adjustable entry port 541 that is movable along a length of the slot 540 to adjust an angle of a suture insertion or implant device or suture that passes therethrough with respect to a central longitudinal axis L'''' of the device 500. As shown, the housing 504 includes an elongate opening or slot 540 formed in an extension 501 that extends radially away from a sidewall 508 of the housing 504, although in other embodiments the slot 540 can be formed in the sidewall 508 itself and/or the extension 501 can be considered to be part of the sidewall 508. The opening 540 can have a variety of shapes and configurations, but in the illustrated embodiment the opening 540 is elongate, having a substantially elliptical shape. An adjustable entry port 541, alternatively referred to herein as an instrument receiving opening or an adjustable sealable opening, is disposed within the elongate opening 540 and has a seal 544 associated therewith. The seal 544 can be disposed at the surface of the extension 501 as shown, or it can be disposed at a location more proximate to the central longitudinal axis L''''. The seal 544 provides a seal between the outside environment and a working channel 522 of the device 500 that is defined by a central lumen 510 of the housing 504 and an interior lumen 520 of the cannula 502. While in earlier embodiments a channel was associated with the various openings 140, 240, 340, 440 that extends through the respective housings 104, 204, 304, 404, no such channel is provided for the trocar 500 so that the rotation of the openings 540 can be more easily achieved. Instead, the openings 540 extend a distance into the housing before opening to openings formed in the rotary disc 590, as described in greater detail below.

The adjustable entry port 541 is configured to receive a suture insertion or implant device and/or suture therethrough, which in turn can be passed through the working channel 522, a sealed opening 560 formed in a sidewall 518 of the cannula 502 that extends distally from the housing 504, and to a surgical site. The sealed opening 560 can be sealed, for example, by having a seal 564 disposed within the opening 560. As described below, the adjustable entry port 541 is movable along a length of the opening 540 to adjust a bite angle at which the insertion device and/or suture disposed therethrough passes through the working channel 522 and into tissue. Although not illustrated, a complimentary extension having an elongate opening or slot and an adjustable entry port, can be formed on an opposed side of the device 500, or at any other location along a circumference of the housing 504.

Figure 9:
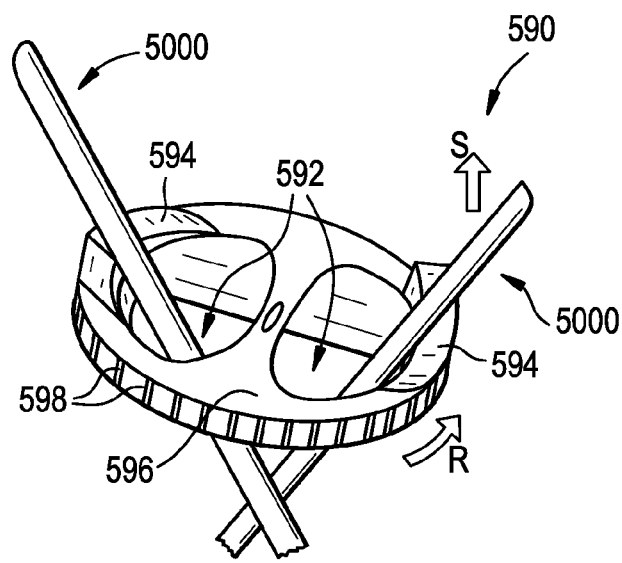
FIG. 9 is a perspective view of the rotary dial of FIG. 8, the rotary dial having multiple suture implant devices disposed therethrough.
Figure 10:
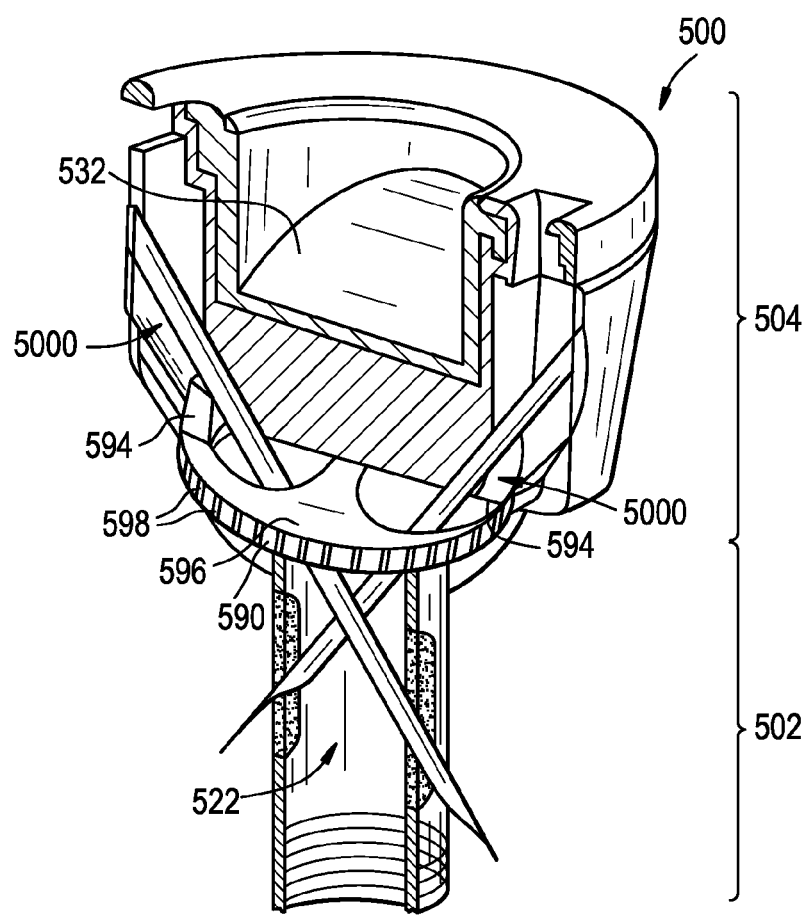
FIG. 10 is a perspective cross-sectional view of the surgical access device of FIG. 8 taken along line D-D, the surgical access device having the suture implant devices of FIG. 9 disposed therethrough.

The adjustable entry port 541 can be moved through the opening 540 using a variety of different techniques, and in the illustrated embodiment a rotary dial 590 is provided to move the adjustable entry port 541. The rotary dial 590, which is illustrated in FIGS. 9 and 10, can be disposed distal of an entrance of the adjustable entry point 541 and distal of a distal-most seal 532 (typically a duckbill or zero-closure seal) disposed in the housing 504, as best seen in FIG. 10. The rotary dial 590 can include one or more receiving openings 592 formed therein for receiving an instrument to pass from the adjustable entry port 541 to the working channel 522. The receiving openings 592 can have diameters or widths that are approximately greater than half a radius of the rotary dial 590 so that a device passing therethrough can be moved through a variety of angles. As shown in FIG. 10, an instrument 5000 can extend from the adjustable entry port 541, through the receiving opening 592, and into the working channel 522.

Turning back to FIG. 9, the rotary dial 590 can further include opposed cams 594 that are disposed on a surface 596 of the rotary dial 590, the cams 594 being ramped to allow for adjustability. A seal spring (not shown) can further be disposed therein to bias the rotary dial 590. In one embodiment, the spring can be biased towards a bottom part of the receiving opening 592 so that rotation of the cam 594 in a direction R biases the rotary dial 590 upward in a direction S, as shown in FIG. 9. Accordingly, as the rotary dial 590 is turned, for example, counterclockwise in the direction R, an instrument 5000 disposed in the opening 592 can slide up the cam 594 in the direction S. Notably, the instrument 5000 is not necessarily disposed in the opening 592 when the dial 590 is rotated, and in such instances, when the device 5000 is eventually passed through the dial 590, then it attains the illustrated configuration set by the rotation of the dial 590.

Figure 8:
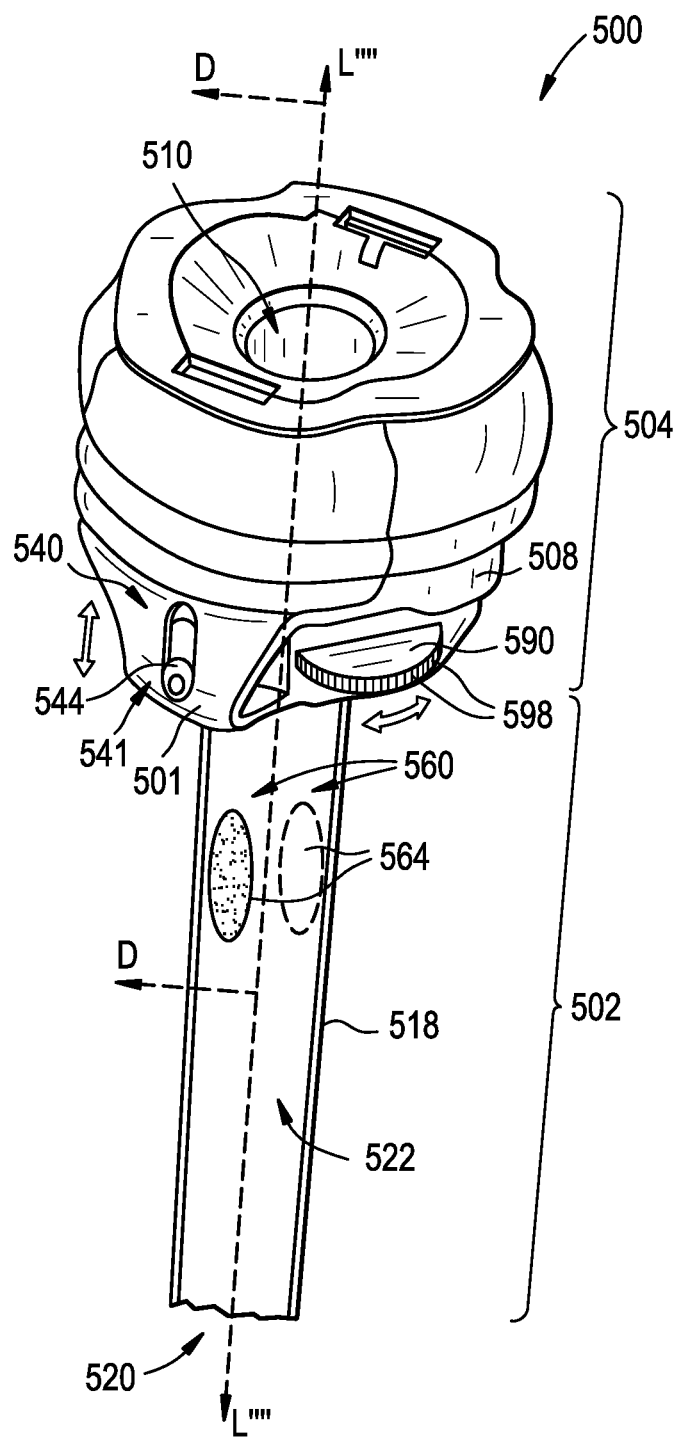
FIG. 8 is a perspective view of still another exemplary embodiment of a surgical access device, the device including multiple elongate ports associated with each of a housing and a cannula of the device, and at least one of the elongate ports of the housing including an adjustable entry point that is controllable with a rotary dial.

As shown in FIG. 8, the rotary dial can be rotated in either direction, which in turn causes the adjustable entry port 541 to move up and down through the elongate opening 540 to establish a bite angle for the suture insertion device and associated suture. Further, the aggressiveness of the curve of the cam 594 can impact the bite angle that is created, with the more aggressive curve creating a greater variation in bite angle. In the illustrated embodiment, the curves of the cams 594 yield a change in bite angle approximately in the range of about 15 degrees to about 45 degrees, and in one non-limiting exemplary embodiment the change in bite angle is about 30 degrees. Further, an outer edge of the rotary dial 590 can include one or more gripping features 598, e.g., ridges, grooves, or the like, to assist a user in being able to easily rotate the dial. In some embodiments, the dial 590 can be configured to have distinct set positions keyed into it such that as the dial 590 is rotated, it moves between various preset, keyed configurations that result in different bite angles.

Figure 11:
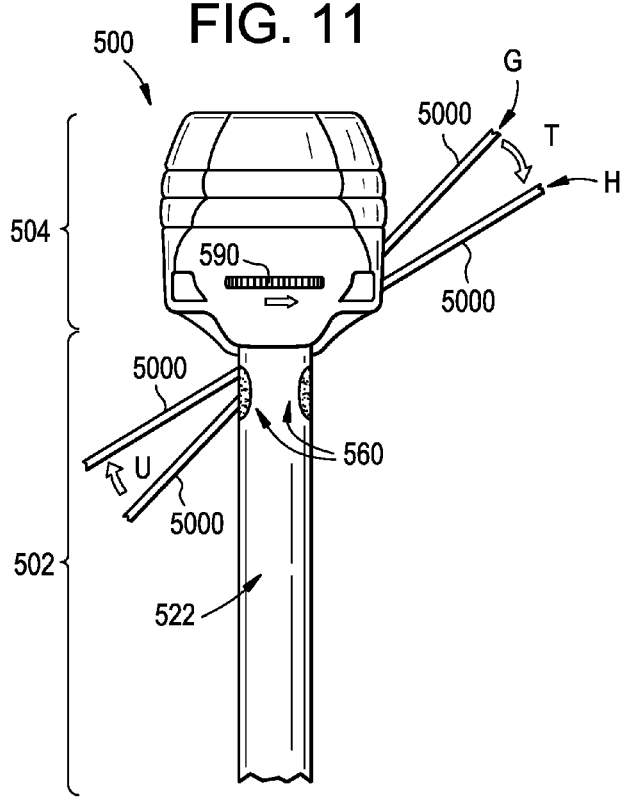
FIG. 11 is a front view of the surgical access device of FIG. 8 illustrating a suture implant device in two different locations.
Figure 12A:
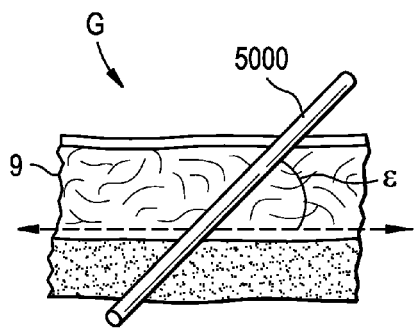
FIGS. 12A and 12B are schematic illustrations of the suture implant device of FIG. 11 disposed at the two different locations, respectively.
Figure 12B:
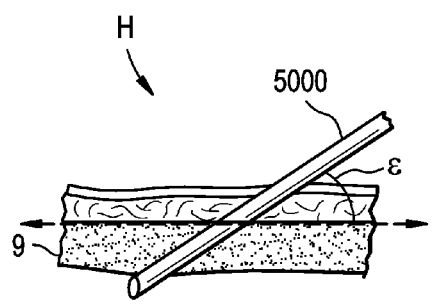

FIG. 11 depicts the adjustable entry point 541 (not visible) being moved by rotation of the rotary dial 590 in the counterclockwise direction R. As shown, as the dial 590 is rotated in the counterclockwise direction R, the portion of the instrument 5000 located proximate to the adjustable entry port 541 moves in a downward direction T, while the portion of the instrument 5000 located proximate to sealed openings 560 of the cannula 502 move in an upward direction U, thereby decreasing the bite angle associated with the instrument 5000. The two different bite angles with respect to tissue 9 are more clearly illustrated in FIGS. 12A and 12B, with an angle ε decreasing in FIG. 12B as the rotary dial 590 is moved in the counterclockwise direction R and the adjustable entry point 541 moves distally through the opening 540 (not visible). In particular, the illustrated embodiment in FIG. 12A is related to the instrument 5000 being disposed in a first position G, and the illustrated embodiment in FIG. 12B being related to the instrument 5000 being disposed in a second position H, with both positions being identified in FIG. 11.

A person skilled in the art will recognize that the components of the surgical access device 500 can be altered to achieve a variety of other configurations, such as rotation in either direction being able to achieve larger and smaller bite angles, having additional openings formed in any of the housing 504, the rotary dial 590, and/or the cannula 502 to provide further flexibility and adjustability, etc. In the illustrated embodiment, an angle of adjustment is approximately in the range of about 15 degrees to about 60 degrees, although smaller and larger angles can be achieved without departing from the spirit of the present disclosure. The angle formed allows different wall thicknesses to be passed through. Accordingly, in view of the present disclosures, a range of wall thicknesses through which an instrument and/or a suture can be passed in view of the provided for surgical access devices is approximately in the range of about 1 centimeter to about 5 centimeters.

Figure 13:
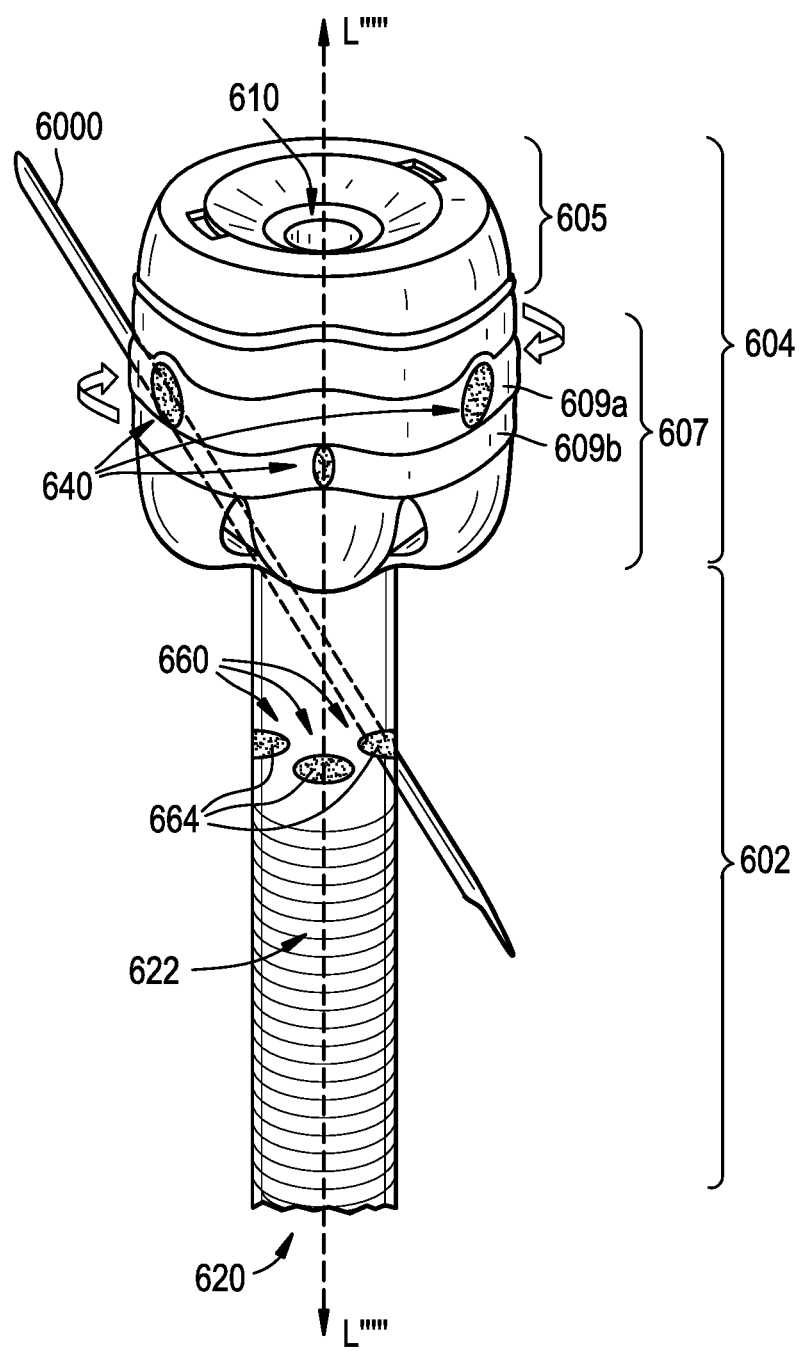
FIG. 13 is a perspective view of another exemplary embodiment of a surgical access device having multiple ports associated with each of a housing and a cannula of the device, as well as a portion of a suture implant device disposed therethrough.
Figure 14:
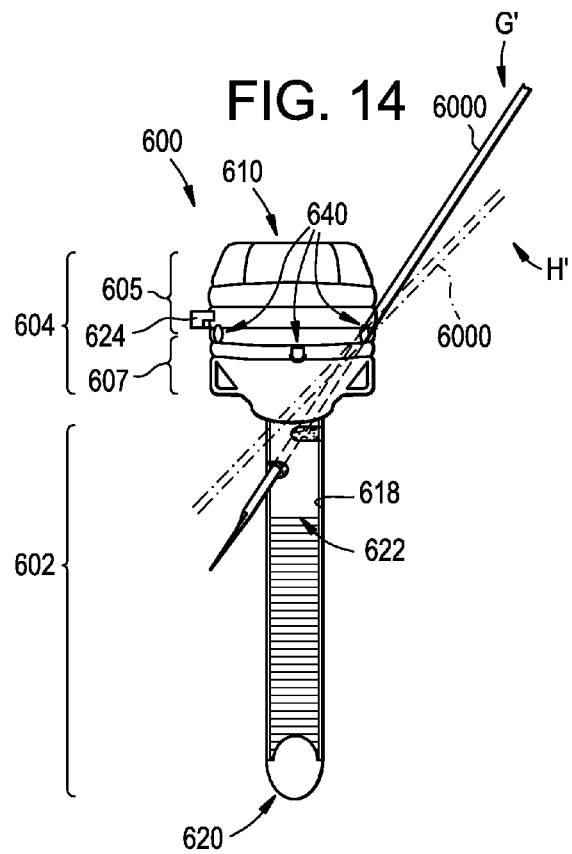
FIG. 14 is a front view of the surgical access device of FIG. 13 illustrating the suture implant device of FIG. 13 in two different locations.
Figure 16:
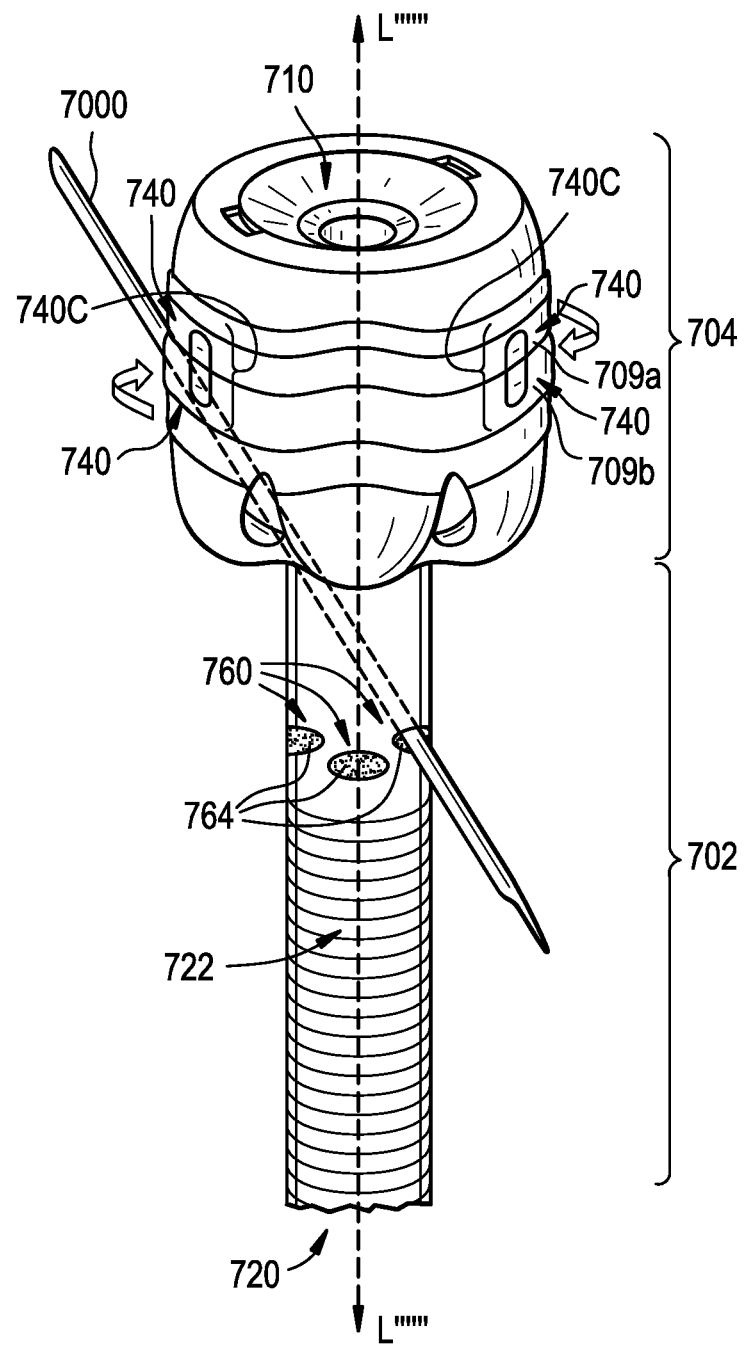
FIG. 16 is a perspective view of yet another exemplary embodiment of a surgical access device having multiple ports associated with each of a housing and a cannula of the device, as well as a portion of a suture implant device disposed therethrough.

Surgical Access Devices with Openings that Rotate with Respect to a Central Longitudinal Axis FIGS. 13 and 14 and FIG. 16 provide two additional embodiments of surgical access devices that both provide multiple openings to achieve different bite angles, and also provide for movement of the openings with respect to respective central longitudinal axes of the surgical access devices to provide additional adjustability options for achieving a variety of bite angles. More particularly, the openings are configured to be rotated about a central longitudinal axis of the surgical access device.

FIGS. 13 and 14 illustrate one exemplary embodiment of a surgical access device, as shown a trocar 600, having openings 640 formed in a housing 604 of the trocar 600 that are adjustable. As shown, the housing 604 includes a plurality of rotatable discs 609a, 609b associated with a distal chamber portion 607 of the housing 604, with a cap portion 605 being removably and replaceably attachable to the distal chamber portion 607. In the illustrated embodiment, an insufflation port 624 is associated with the cap portion (FIG. 14), and the two rotatable discs 609a, 609b are associated with the distal chamber portion 607. Each disc 609a, 609b can include one or more openings 640 formed therein. The openings 640 can extend towards a central longitudinal axis L'''' in a manner similar to the openings 540 described above with respect to the device of FIGS. 8-11. Although not illustrated, a rotary disc can be provided below the rotary discs 609a, 609b and can operate in a manner similar to the rotary disc 590 described above, and thus a channel or path can be formed between the openings 640, through the openings formed in such a rotary disc, and to a working channel 622 of the trocar, the working channel 622 being defined by a central lumen 610 of the housing 604 and an inner lumen 620 of the cannula 602.

Figure 15A:
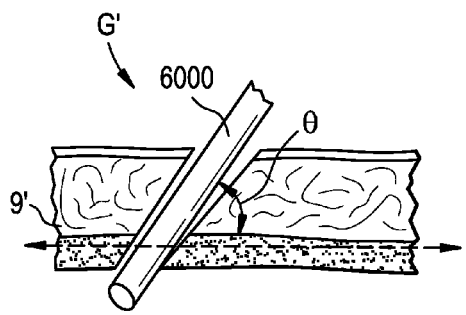
FIGS. 15A and 15B are schematic illustrations of the suture implant device of FIG. 14 disposed at the two different locations, respectively.
Figure 15B:
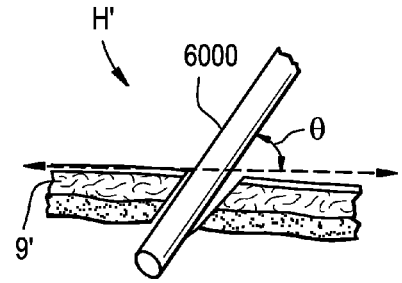

In view of the present disclosures, any of the plurality of housing openings 640 can be rotated and used in conjunction with any of the plurality of cannula openings 660 to achieve various bite angles. FIG. 14 provides one illustration of an insertion instrument 6000 having a different bite angle by virtue of being disposed in openings 640 of different rotary discs 609a, 609b. However, a person skilled in the art will also recognize that as any of the discs 609a, 609b rotates, and the instrument 6000 can be used in conjunction with other openings 660 in the cannula 602, the same housing opening 640 can be used to create a different bite angle as well just by virtue of the disc 609a, 609b in which the instrument 6000 is disposed rotating. As shown, the instrument 6000 has a first bite angle when the instrument 6000 is disposed in an opening disposed in the top rotary disc 609a and is passed through an elongate sealed opening 660 formed in the cannula 602, while the instrument 6000 has a second bite angle when the device 6000 is disposed in an opening 640 disposed in the bottom rotary disc 609b and is passed through a different elongate sealed opening 660 formed in the cannula 602. Notably, the elongate sealed openings 660 provided for in a sidewall 618 of the cannula 602 of FIG. 14 are elongate along a width rather than a length, although as described above, either configuration is acceptable. Seals 664 can be associated with the openings 660 as described in greater detail in other embodiments. The achieved bite angles θ of both configurations are illustrated with respect to tissue 9' in FIGS. 15A and 15B, with the illustrated embodiment in FIG. 15A being related to the instrument 6000 being disposed in a first position G', and the illustrated embodiment in FIG. 15B being related to the instrument 6000 being disposed in a second position H', with both positions being identified in FIG. 14.

FIG. 16 depicts an alternative embodiment of a surgical access device, as shown a trocar 700, having rotary discs 709a, 709b. Similar to the surgical access device of FIGS. 13 and 14, a plurality of discs, as shown the two discs 709a, 709b, are included as part of a housing 704 of the trocar 700, and each disc 709a, 709b includes a plurality of openings 740 formed therein. In the embodiment illustrated in FIGS. 13 and 14, the openings 740 formed in the discs 609a, 609b had a portion of an outer wall of the respective discs 609a, 609b disposed around an entirety of each opening 640. In contrast, the openings 740 formed in the discs 709a, 709b include at least one opening 740 that is open-ended such that the open-ended openings 740 can be moved to an alignment position in which one opening 740 associated with one disc 709a is aligned with one opening 740 associated with the other disc 709b to form an elongate opening 740C. A suture insertion or implant instrument 7000 and/or suture can then be passed through any portion of the formed elongate opening 740C, into a working channel 722 of the trocar 700 that is formed by a central lumen 710 of the housing 704 and an interior lumen 720 of the cannula 702, through openings 760 formed in a sidewall 718 of the cannula 702, and to a surgical site.

In the illustrated embodiment, multiple elongate openings 740C are formed at the same time, although the openings 740 on each disc 709a, 709b do not need to be spaced in such a manner. In some instances, only a single elongate opening 740C is formed when two openings 740 are disposed in an alignment position with respect to each other. Further, when an opening 740 formed in one disc 709a is not aligned with an opening 740 formed in an adjacent disc 709b, a surface of the adjacent disc 709b closes the opening 740 of the first disc 709a such that the opening 740 can be used to receive a suture insertion or implant instrument and/or suture as described herein. Either or both of the discs 709a, 709b can rotate about a central longitudinal axis L'''' of the surgical access device 700 to selectively move one or more openings 740 of a disc 709a, 709b into and out of an alignment position.

Similar to other embodiments, the one or more sealed openings 760 can be formed in a sidewall 718 of the cannula 702. In the illustrated embodiment, there are three openings 760 illustrated, each being elongate along a horizontal plane that is substantially perpendicular to the central longitudinal axis L'''' (the plane going into and out of the paper as shown), with a central vertex 760c being more distal than two aligned proximal vertices of a sealed opening triangular configuration. Seals 764 can be associated with the openings 760 as described in greater detail in other embodiments. Further, although the illustrated embodiments provide for two rotary discs having openings associated therewith, fewer or more rotary discs can be incorporated into the housing of any surgical access device without departing from the spirit of the present disclosure.

One useful and independently novel aspect of the present disclosure is the ability it provides a user to selectably adjust a bite angle formed between a suture path extending between one or more openings associated with a housing of a surgical access device and one or more openings associated with a cannula of the surgical access device. Whether the ability to adjust is a result of the inclusion of multiple openings in association with the housing or cannula, the ability to move the openings with respect to a central longitudinal axis of the surgical access device (e.g., rotate about the central longitudinal axis by way of one or more rotary discs), the ability to move an adjustable entry port within an elongate seal, the ability to operate a rotary dial to move an adjustable entry port or openings more generally, or any other adjustable feature afforded by the present disclosures, the selectable adjustment enhances a surgical procedure because it allows a user to manipulate the angle at which a suture will enter tissue so that the opening in which the surgical device is inserted can be closed in a desirable manner.

Seals and Sealed Openings of the Cannula

Figure 17:
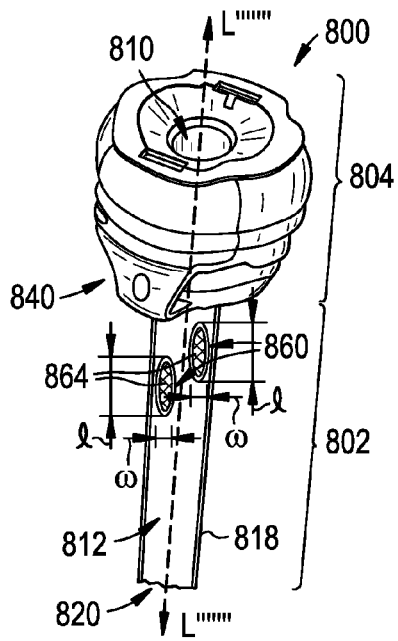
FIG. 17 is a perspective view of another exemplary embodiment of a surgical access device, the device including multiple elongate ports associated with a cannula of the device.

FIG. 17 provides for another exemplary embodiment of a surgical access device, as shown a trocar 800. Similar to previous embodiments, the trocar 800 includes a housing 804 having a cannula 802 extending distally therefrom, and one or more openings 840, 860 are associated with each of the housing 804 and cannula 802, respectively, to allow for a path to be formed through which a suture insertion or implant instrument and/or suture can travel from an outside environment, through the housing 804, through a working channel 822 of the device 800 defined by a central lumen 810 of the housing 804 and an interior lumen 820 of the cannula 802, through the cannula 802, and to a surgical site. The focus of this embodiment is on the sealed openings 860 formed in the cannula 802, which are illustrated in greater detail in FIGS. 18A and 18B. As shown in FIG. 17, two opposed sealed openings 860 are formed in a sidewall 818 of the cannula 802. Each opening 860 is elongate and generally elliptical in shape. A length l of the sealed openings 860 in a direction substantially along an axis Y that is parallel to a central longitudinal axis L'''' of the device is greater than a width w of the sealed openings 860. Each sealed opening 860 is formed by forming a lumen in the sidewall 818 and associating a seal 864 with the lumen. In various embodiments the seal 864 can be positioned within the lumen or overtop of the lumen. As shown, the seal 864 is sized to sit snuggly within the lumen so that fluid does not generally pass between the seal 864 and the portion of the sidewall 818 that defines the lumen.

Figure 18A:
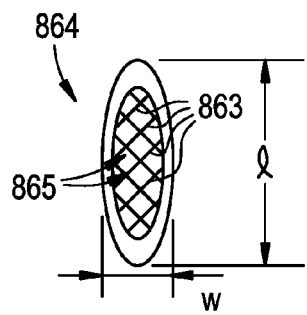
FIG. 18A is front view of a seal associated with the elongate ports of FIG. 17.
Figure 18B:
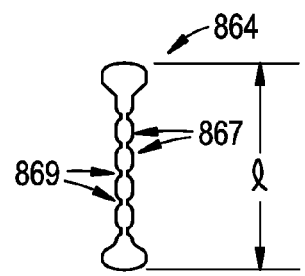
FIG. 18B is a side view of the seal of FIG. 18A.
Figure 19A:
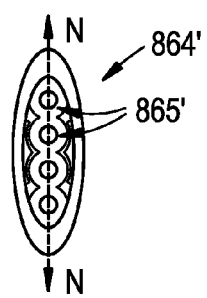
FIG. 19A is front view of one exemplary embodiment of a seal that can be used in conjunction with the elongate ports of FIG. 17.
Figure 19B:
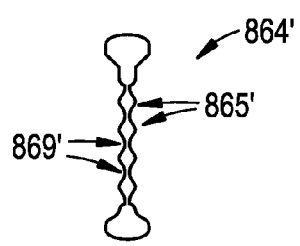
FIG. 19B is a side view of the seal of FIG. 19A.

As shown in FIGS. 17, 18A, and 18B, the seal 864 includes a plurality of ridges 863 formed in a surface that faces towards the working channel 822 of the trocar 800. The ridges 863 are in a criss cross pattern such that openings 865, also referred as pre-defined tear zones, are formed between the ridges 863. One or more of the openings 865 can be configured to have an instrument, e.g., a suture insertion or implant device, and/or suture passed therethrough and seal around the instrument and/or suture to maintain a seal between the working channel 822 and a surgical site. The ridges 863 provide both a pre-defined path to which the instrument and/or suture can be directed, and also provide reinforcement for the seal so that remnants of the seal 864 are not separated from the rest of the seal as an instrument and/or seal are passed through the seal. Further, as illustrated best by FIG. 18B, the ridges 863 form individual pockets 867 along a length of the seal 864 with narrowed neck portions 869 between each pocket 867, thus providing individual, predefined openings 865 through which instruments and/or sutures can be disposed. Additionally, the preformed patterns minimize an amount of load that needs to be applied to an instrument and/or suture being passed through the seal 864.

FIGS. 19A-20B illustrate two further, non-limiting embodiments of seals 864', 864" having patterned guide surfaces that can be associated with the elongate openings 860 of FIG. 17. The seal 864' of FIGS. 19A and 19B includes a patterned guide surface that has a plurality of pre-formed openings or tear zones 865' centrally disposed along a longitudinal axis N of the seal 864'. As with the seal 864, the patterned guide surfaces minimize an amount of load that needs to be applied to an instrument and/or suture being passed through the seal 864'. The longitudinal axis N is substantially parallel to the central longitudinal axis L''''' of the surgical access device 800 when the seal 864' is disposed within the opening 860. Each of the four pre-formed openings 865' is configured to be closed when no instrument or suture is disposed therethrough, and is configured to seal around and instrument and/or suture that is disposed therethrough. Each pre-formed opening 865' can independently open and close apart from the other pre-formed openings 865'. Similar to the seal 864 as best shown in FIG. 19B, a narrowed neck portion 869' can extend between each of the openings 865' to provide individual, predefined openings through which instruments and/or sutures can be disposed. The material disposed around each opening can help reinforce the seal so that portions surrounding each opening 865' do not break away from the seal 864' when an instrument is passed therethrough. Further, the seal 864' can be generally flexible in six degrees, thereby allowing an instrument disposed through one opening 865' to be moved with some level of freedom in two directions longitudinally, horizontally, and through the seal 864'. Accordingly, while the selection of which opening 865' an instrument and/or suture is passed can impact the associated bite angle, the bite angle can also be adjusted when such instrument and/or suture is disposed in a single opening 865' due to the flexibility of the seal 864'.

Figure 20A:
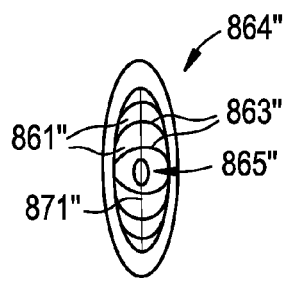
FIG. 20A is front view of another exemplary embodiment of a seal that can be used in conjunction with the elongate ports of FIG. 17.
Figure 20B:
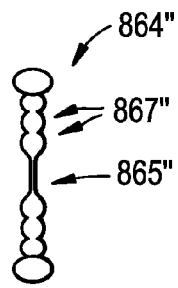
FIG. 20B is a side view of the seal of FIG. 20A.

FIGS. 20A and 20B illustrate an alternative embodiment of a seal 864" that includes a patterned guide surface with at least one pre-formed opening 865" formed therein. As shown, a preformed opening or tear zone 865" can be formed centrally in the seal 864", with a plurality of radial arcs 861" disposed above and below the preformed opening 864'. The seal 864" is generally configured to allow an instrument and/or suture associated with the instrument to be passed through the central opening 865", and the arcs 861" can provide flexibility to allow the instrument and/or suture passing therethrough to be manipulated to achieve various bite angles. The arcs 861" also provide reinforcement for the seal 864" so that portions surrounding the opening 865" do not break away from the seal 864" when an instrument is passed therethrough. A longitudinal slit 871" can extend along a length of the seal 864", thereby providing the ability to insert an instrument and/or a suture through any of the arcs 861" as well. Slits 863" disposed between each arc 861" can help form individual pockets 867" through which an instrument and/or suture can be disposed, as illustrated in FIG. 20B.

Figure 21:
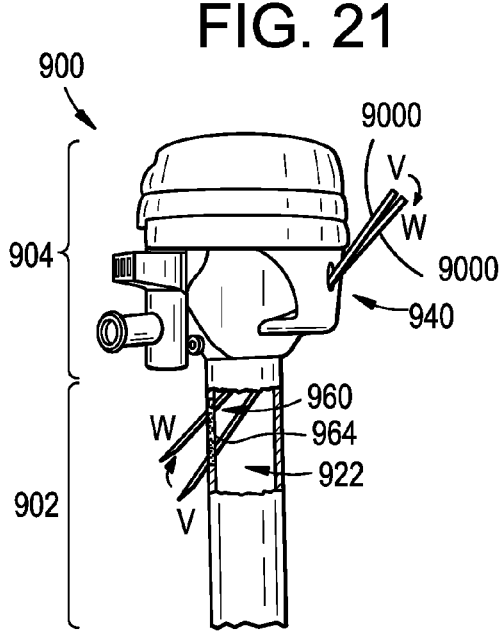
FIG. 21 is a front view of still another exemplary embodiment of a surgical access device, the device including a slidable, floating seal associated with a cannula of the device and having a suture implant device disposed therein in two different locations.
Figure 22A:
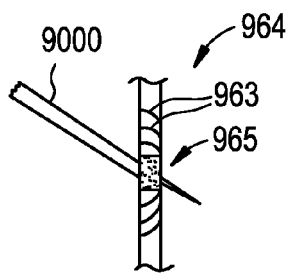
FIG. 22A is a schematic side view of the slidable, floating seal and the suture implant device of FIG. 21, the suture implant device being disposed in a resting position.
Figure 22B:
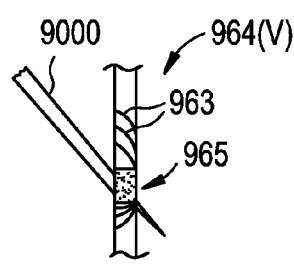
FIG. 22B is a schematic side view of the slidable, floating seal and the suture implant device of FIG. 22A, the suture implant device being disposed in a first position.
Figure 22C:
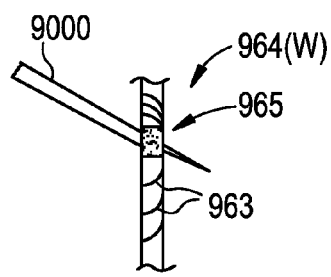
FIG. 22C is a schematic side view of the slidable, floating seal and the suture implant device of FIG. 22A, the suture implant device being disposed in a second position.

FIGS. 21-22C illustrate an exemplary embodiment of a movable seal associated with a sidewall of a cannula of a surgical access device. As shown in FIG. 21, a surgical access device, e.g., a trocar assembly 900, includes a housing 904 and a cannula 902 extending distally therefrom. One or more openings 940, 960 are associated with each of the housing 904 and the cannula 902. Further, a movable seal 964 is disposed within one opening 960 formed in a sidewall 918 of the cannula 902. The movable seal 964 includes a slidable, floating instrument entrance 965 that allows a bite angle to be adjusted when a suture insertion or implant instrument and/or suture is disposed therethrough. In an unengaged state, the slidable, floating resealable instrument entrance 965 can be substantially centered with respect to the seal 964, and thus the opening 960. When no instrument is disposed therethrough, the slidable, floating resealable instrument entrance 965 maintains a seal between a working channel 922 defined by a central lumen 910 of the housing 904 and an inner lumen 920 of the cannula 902, and an outside environment. A plurality of slits 963 can be formed in a surface of the seal 964 to assist in providing flexibility in the seal 964. An instrument 9000 can be passed into the instrument entrance 965, as shown in FIG. 22A, such that the seal 964 forms a seal around the instrument 9000. The instrument can be manipulated between first and second positions V and W as labeled in FIG. 21 and as illustrated in FIGS. 22B and 22C, respectively. During manipulation, a seal is maintained around the instrument 9000, as shown in FIGS. 22B and 22C, so that fluid does not pass across the seal 964. Similar to the earlier embodiments, the pre-defined, pre-formed nature of the slidable, floating instrument entrance 965 and associated seal 964 minimizes an amount of load that needs to be applied to an instrument and/or suture being passed through the seal 964, while also minimizing the risk of a remnant of the seal body becoming dislodged from the seal 964.

While the construction of the seals provided for herein can themselves lead to flexible seals that permit a bite angle to be adjusted while reducing the risk of remnants becoming separated from the seal, the materials used to form the seals can also assist in providing flexibility and a decreased risk of remnant dislodging. Thus, materials that are stretchable and tear-resistant are well-suited for use in formed sealed openings in the cannula and/or the housing. Some non-limiting examples of materials that can be used to form the seals include various elastomers and rubbers, such as polyisoprene, Butyl rubber, anionically polymerized isoprene (e.g., Kraton® as manufactured by Kraton Polymers of Houston, Tex.), polyurethane, silicone, and other similar materials. One or more materials can be used to form any of the seals provided for herein.

The particular seal constructions provided for herein are useful and independently novel aspects of the present disclosure. The seals provide pre-defined rupture locations that minimize tear remnants that are left behind, which is particularly useful for seals formed in a sidewall of a cannula of a surgical access device. A person skilled in the art will recognize that the seals provided for herein can also be used effectively in other types or portions of medical devices, as well as other fields that use seals in which the present disclosures will prove useful.

Seal Sleeve

Figure 23:
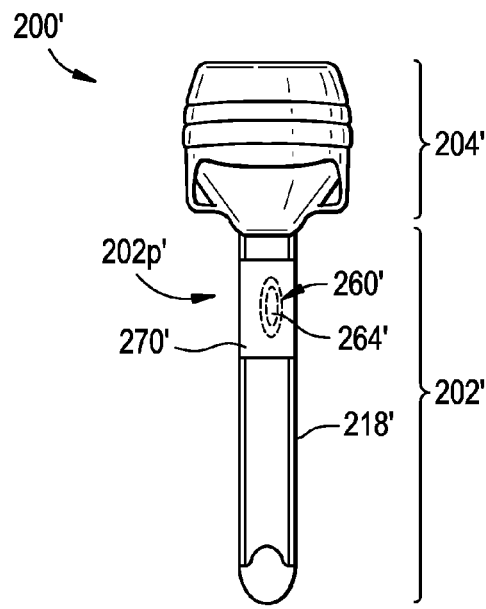
FIG. 23 is a side view of another exemplary embodiment of a surgical access device, the device including a sleeve that is used to provide a seal associated with a cannula of the device.
Figure 24:
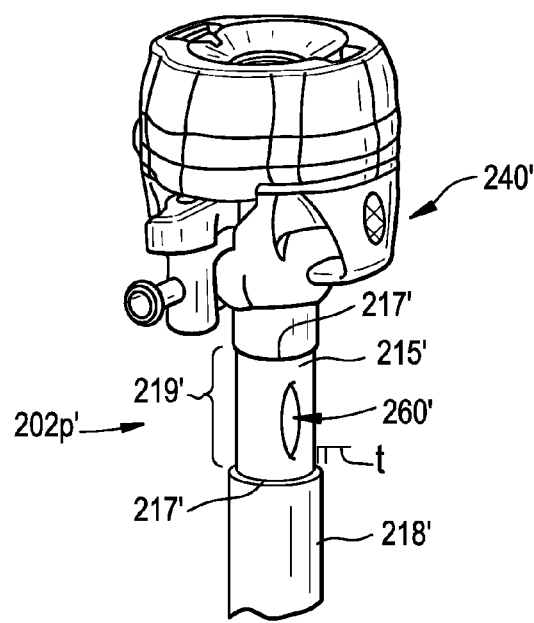
FIG. 24 is a perspective view of the surgical access device of FIG. 23, the device having the sleeve removed from the cannula to expose an opening formed in the cannula.
Figure 25:
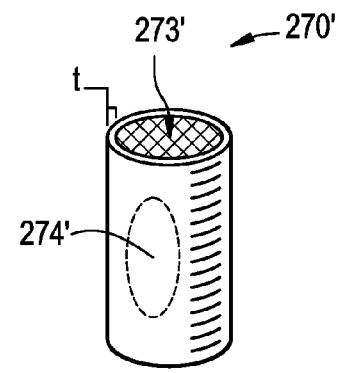
FIG. 25 is a perspective view of the sleeve of FIG. 23.

The surgical access device 200 of FIGS. 5A-5E includes a seal sleeve 270 disposed around openings 260 formed in the sidewall 218 of the cannula 202 to create a sealed opening. In that embodiment, however, the thickness of the sleeve 270 causes a diameter of the cannula 202 as a whole to be greater at the location of the sleeve 270 than elsewhere along a length of the cannula 202. FIGS. 23-25 provide for an alternative embodiment in which a cannula 202' of a surgical access device, e.g., a trocar assembly 200', is modified to accommodate a thickness of a sleeve 270' so that a diameter of the cannula 202' is not necessarily greater at the portion of the cannula 202' that includes the sealed openings 260' and sleeve 270'.

As shown in FIGS. 23 and 24, a surgical access device, e.g., a trocar assembly 200', includes a housing 204' and a cannula 202' extending distally therefrom. Each of the housing 204' and cannula 202' can include at least one opening 240', 260', respectively, associated therewith for passing a suture insertion or implant instrument and/or suture therethrough as described above. The opening(s) 260' in the cannula 202' can be formed in a proximal portion 202p' of the cannula 202'. In the illustrated embodiment, there are two opposed openings 260' formed in the cannula 202', although only one is visible. Like the other embodiments provided for, however, any number of openings 260' can be formed in a sidewall 218' of the cannula 202', at most any location and in any number of configurations or patterns.

As described at least with respect to FIGS. 5A-5E, a seal sleeve 270' having one or more pre-formed seals 274' can be used in conjunction with the openings 260' to form a sealed opening that is configured to prevent fluid from passing through the opening 260' when no instrument or the like is disposed in the seal 264', and which can seal around an instrument or the like passed through the seal 264'. In other embodiments of a sleeve, no pre-formed seal is formed and the sleeve itself is configured to generally form a seal around an instrument and/or suture passing therethrough, but maintain a seal when nothing is passed therethrough.

One exemplary embodiment of a seal sleeve 270' is illustrated in FIG. 25. The seal sleeve 270' is generally cylindrical in shape and includes a lumen 273' extending therethrough. The lumen 273' is generally sized to allow the sleeve 270' to be elastically coupled to the cannula 202' when the sleeve 270' is disposed around or on the cannula 202'. In particular, the seal sleeve 270' can be configured to stretch and snap along any portion of the cannula 202' wherein openings 260' designed to have seals associated therewith are disposed on the cannula 202'. The sleeve 270' can have any number of configurations associated with it, including the pre-formed openings 264' and/or patterned surfaces described above, and it can be made from materials known to those skilled in the art for providing sealing characteristics, e.g., various elastomers and rubbers, such as polyisoprene, Butyl rubber, anionically polymerized isoprene (e.g., Kraton® as manufactured by Kraton Polymers of Houston, Tex.), polyurethane, silicone, and other similar materials. One or more materials can be used to form any of the seals provided for herein.

As shown in FIG. 24, a portion of the proximal portion 202p' can have a portion 219' of the sidewall 218' removed to accommodate placement of the seal sleeve 270' over the openings 260' without increasing a diameter of the device 200' at the portion that includes both the cannula 202' and the sleeve 270'. As shown in FIG. 25, the sealing sleeve 270' has a thickness t, and as shown in FIG. 24, the portion 219' of the sidewall 218' that is removed results in a recess 215' disposed between two ledges 217', each ledge 217' being sized to approximately have the same thickness t as the sleeve 270'. The shape of the recess 215' is such that it is complimentary to the shape of the seal sleeve 270', and thus in the illustrated embodiment it is substantially cylindrical in shape. When the seal sleeve 270' is placed in the recess 215', the seal sleeve 270' can sit approximately flush with the rest of the cannula 202' such that an outer wall of the seal sleeve 270' is approximately aligned with the outer sidewall 218' of the cannula 202'. While the thickness t of the seal sleeve 270', and thus the thickness t of the ledges 217', can depend on a variety of factors, including the size of the cannula (e.g., a thickness of the cannula, which in some embodiments is about 0.8 millimeters), the patient, and the preferences of the surgeon, in some exemplary embodiments the thickness t can be approximately in the range of about 0.05 millimeters to about 0.5 millimeters, more specifically in some embodiments approximately in the range of about 0.1 millimeters to about 0.3 millimeters, and in one non-limiting embodiment the thickness t is about 0.4 millimeters.

A person skilled in the art will recognize that the various features provided for across the various embodiments can be used interchangeably across other embodiments without departing from the spirit of the present disclosure. By way of non-limiting example, to the extent one embodiment includes an elongate opening and another embodiment does not, the elongate opening can be easily incorporated into the other embodiment. The ability to transpose one or more features from one embodiment to any other embodiment is readily understandable in view of the present disclosures. In no way is the depiction of one feature in one embodiment limiting of that feature only being able to be implemented in that embodiment.

Further, a person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the disclosure based on the above-described embodiments. Accordingly, the disclosure is not to be limited by what has been particularly shown and described, except as indicated by the appended claims. Additionally, while the present disclosures generally discuss passing suture insertion or implant devices and sutures through the paths formed between openings of the housing and openings of the cannula, a person skilled in the art, in view of the present disclosures, would understand that other devices, instruments, and the like can be passed between the openings and other features of the surgical access device without departing from the spirit of the present disclosure. All publications and references cited herein are expressly incorporated herein by reference in their entirety.

What is claimed is:
1. A surgical access device, comprising:
   (a) a housing having a top surface, a central lumen extending therethrough, and a sidewall disposed around the central lumen, the sidewall defining a side surface of the housing, the housing having at least one opening extending transversely through the side surface, the at least one opening having an opening seal associated therewith;
   (b) a cannula extending distally from the housing and in fluid communication with the central lumen to define a working channel that is sized and configured to receive a surgical instrument, the cannula having at least one sealed opening extending transversely through a sidewall thereof; and
   (c) a seal disposed within the working channel and configured to seal the working channel when no surgical instrument is disposed therethrough,
   wherein the at least one opening of the housing is radially outward of the at least one sealed opening of the cannula,
   wherein the at least one opening of the housing and the at least one sealed opening of the cannula communicate directly and transversely with the working channel, wherein the at least one opening of the housing defines a proximal-most transverse opening to the working channel,
   wherein the at least one opening of the housing and the at least one sealed opening of the cannula are configured to form a suture path such that a suture can be passed from an outside environment, through the at least one opening of the housing, across the working channel, through the at least one sealed opening of the cannula, and to a surgical site.

2. The device of claim 1, wherein the at least one opening of the housing and the at least one sealed opening extending through the sidewall of the cannula are configured such that an angle formed between a central longitudinal axis extending through the cannula and an axis extending between the at least one opening of the housing and the at least one sealed opening extending through the sidewall of the cannula is adjustable.

3. The device of claim 2, wherein the at least one opening of the housing comprises a plurality of openings extending through the side surface of the housing, each opening having a seal associated therewith, and wherein the angle is adjustable as a result of the axis extending between the at least one opening of the housing and the at least one sealed opening extending through the sidewall of the cannula having a first position at which the axis extends between a first opening of the plurality of openings extending through the side surface of the housing and an opening of the at least one sealed opening extending through the side surface of the cannula, and a second position at which the axis extends between a second opening of the plurality of openings extending through the sidewall of the housing and the opening of the at least one sealed opening extending through the sidewall of the cannula.

4. The device of claim 2, wherein the at least one sealed opening extending through the sidewall of the cannula comprises a plurality of sealed openings extending through the sidewall of the cannula, and
wherein the angle is adjustable as a result of the axis extending between the at least one opening of the housing and the at least one sealed opening extending through the sidewall of the cannula having a first position at which the axis extends between an opening of the at least one opening of the housing and a first sealed opening of the plurality of sealed openings extending through the sidewall of the cannula, and a second position at which the axis extends between the opening of the at least one opening of the housing and a second sealed opening of the plurality of sealed openings extending through the sidewall of the cannula.

5. The device of claim 2, wherein the at least one opening of the housing comprises an elongate opening having an elongate length that extends substantially parallel to the central longitudinal axis, the elongate opening comprising an adjustable entry point movable along the elongate length to adjust the angle formed between the central longitudinal axis extending through the cannula and the axis extending between the elongate opening and the at least one sealed opening extending through the sidewall of the cannula.

6. The device of claim 2, wherein the housing comprises:
(i) a first rotary disc having a first opening of the at least one opening of the housing disposed thereon, the first rotary disc being configured to rotate about the central longitudinal axis extending through the cannula; and
(ii) a second rotary disc disposed distal of the first rotary disc and having a second opening of the at least one openings of the housing disposed thereon, the second rotary disc being configured to rotate about the central longitudinal axis extending through the cannula,
wherein the first and second openings are movable to adjust the angle formed between the central longitudinal axis extending through the cannula and the axis extending between the at least one opening of the housing and the at least one sealed opening extending through the sidewall of the cannula.

7. The device of claim 6, wherein the first and second openings are configured to be moved to an alignment position in which the first and second openings are aligned to form an elongate opening having an elongate length that extends substantially parallel to the central longitudinal axis, the elongate opening being configured to allow for multiple entry points of a surgical instrument to thereby provide the adjustable angle formed between the central longitudinal axis extending through the cannula and the axis extending between the at least one opening extending through the sidewall of the housing and the at least one sealed opening extending through the sidewall of the cannula.

8. The device of claim 2, further comprising a rotary dial configured to move the at least one opening of the housing to adjust the angle formed between the central longitudinal axis extending through the cannula and the axis extending between the at least one opening of the housing and the at least one sealed opening extending through the sidewall of the cannula.

9. The device of claim 1, wherein the at least one sealed opening extending through the sidewall of the cannula comprises a seal having a patterned guide surface facing towards the working channel and configured to direct a surgical instrument through one or more pre-defined resealable openings of the seal.

10. The device of claim 9, wherein the patterned guide surface provides a slidable, floating instrument entrance that allows an angle formed between a central longitudinal axis extending through the cannula and an axis extending between the at least one opening of the housing and the at least one sealed opening extending through the sidewall of the cannula to be adjustable.

11. The device of claim 1, wherein a proximal portion of the cannula has a portion of the sidewall that is thinner than surrounding portions of the sidewall of the cannula, the thinner portion having the at least one sealed opening extending therethrough, and
wherein the device further comprises a sealing sleeve sized to be disposed over the thinner portion such that an outer diameter of the combination of the thinner portion of the sidewall and the sealing sleeve is substantially similar to an outer diameter of the surrounding portions of the sidewall of the cannula, the sealing sleeve providing the sealable nature of the at least one sealed opening.

12. The device of claim 1, wherein the at least one opening of the housing defines an entry channel that communicates with the working channel, wherein the entry channel extends outwardly from the sidewall of the housing.

13. The device of claim 1, wherein the suture path is contained within an interior of the surgical access device, wherein the suture path includes a proximal entry end defined by the at least one opening extending through the sidewall of the housing, and a distal exit end defined by the at least one sealed opening extending through the sidewall of the cannula.

14. A surgical access device, comprising:
(a) a housing having a top surface and a side surface;
(b) a cannula extending distally from the housing, the housing and the cannula defining a working channel extending therethrough that is sized and configured to receive a surgical instrument;
(c) a seal disposed within the working channel and configured to seal the working channel when no instrument is disposed therethrough;
(d) at least one entry port, wherein the at least one entry port opens to the working channel through the side surface of the housing; and
(e) at least one exit port, wherein the at least one exit port opens to the working channel through a sidewall of the cannula,
wherein the side surface of the housing is positioned radially outward of the sidewall of the cannula such that the at least one entry port is positioned radially outward of the at least one exit port,
wherein the at least one entry port and the at least one exit port cooperate to define a suture path that extends across the working channel.

15. The device of claim 14, wherein the at least one entry port includes a first seal, wherein the at least one exit port includes a second seal.

16. The device of claim 14, wherein the at least one entry port comprises a plurality of entry ports, and
wherein the suture path extends along a suture path axis that defines an angle relative to a central axis of the cannula, wherein the angle is adjustable as a result of the suture path axis having a first position at which the suture path axis extends between a first entry port of the plurality of entry ports and an exit port of the at least one exit port, and a second position at which the suture path axis extends between a second entry port of the plurality of entry ports and the exit port of the at least one exit port.

17. The device of claim 14, wherein the at least one exit port comprises a plurality of exit ports extending through the sidewall of the cannula, and
wherein the suture path extends along a suture path axis that defines an angle relative to a central axis of the cannula, wherein the angle is adjustable as a result of the suture path axis having a first position at which the suture path axis extends between an entry port of the at least one entry port and a first exit port of the plurality of exit ports, and a second position at which the suture path axis extends between the entry port of the at least one entry port and a second exit port of the plurality of exit ports.

18. The device of claim 14, wherein the suture path extends along a suture path axis that defines an angle relative to a central axis of the cannula, wherein the at least one entry port comprises an elongate opening having an elongate length that extends substantially parallel to the central axis, the elongate opening comprising an adjustable entry point movable along the elongate length to adjust the angle.

19. The device of claim 14, wherein the suture path extends along a suture path axis that defines an angle relative to a central axis of the cannula, wherein the housing comprises:
(i) a first rotary disc having a first entry port of the at least one entry port, the first rotary disc being configured to rotate about the central axis; and
(ii) a second rotary disc disposed distal of the first rotary disc and having a second entry port of the at least one entry port, the second rotary disc being configured to rotate about the central axis,
wherein the first and second entry ports are movable to adjust the angle.

20. The device of claim 19, wherein the first and second entry ports are configured to be moved to an alignment position in which the first and second entry ports align to form an elongate opening having an elongate length that extends substantially parallel to the central axis.

21. The device of claim 14, wherein the suture path extends along a suture path axis that defines an angle relative to a central axis of the cannula, wherein the device further comprises a rotary dial configured to move the at least one entry port to adjust the angle.

22. The device of claim 14, wherein the at least one exit port comprises an exit port seal having a patterned guide surface facing towards the working channel and configured to direct a surgical instrument through one or more predefined resealable openings of the exit port seal.

23. The device of claim 22, wherein the suture path extends along a suture path axis that defines an angle relative to a central axis of the cannula, wherein the patterned guide surface provides a slidable, floating instrument entrance that allows the angle to be adjustable.

24. The device of claim 14, wherein a distal portion of the cannula has a first sidewall thickness, wherein a proximal portion of the cannula has a second sidewall thickness that is less than the first sidewall thickness, wherein the at least one exit port extends through the proximal portion, and
wherein the device further comprises a sealing sleeve sized to be disposed over the proximal portion such that the sealing sleeve is flush with the distal portion, wherein the sealing sleeve is configured to seal the at least one exit port.

25. The device of claim 14, wherein the suture path is contained within an interior of the surgical access device, wherein the suture path includes a proximal entry end defined by the at least one entry port and a distal exit end defined by the at least one exit port.

26. A surgical access device, comprising:
(a) a housing having a top surface and a side surface;
(b) a cannula extending distally from the housing, wherein the cannula includes a central lumen that communicates with an interior of the housing to define a working channel that extends along a central axis of the surgical access device, wherein the working channel is configured to receive a surgical instrument therethrough;
(c) an entry port that communicates with the working channel through the side surface of the housing; and
(d) an exit port that communicates with the working channel through a side portion of the cannula,
wherein the side surface of the housing is radially outward of the side portion of the cannula,
wherein the entry port and the exit port cooperate to define a suture path that extends continuously through an interior of the surgical access device such that the suture path extends from the entry port, across the working channel, and to the exit port without passing through an outside environment.

27. The device of claim 26, wherein the entry port and the exit port are arranged such that the suture path extends obliquely relative to the central axis.

* * * * *